US006635287B2

(12) United States Patent
Soudant et al.

(10) Patent No.: US 6,635,287 B2
(45) Date of Patent: Oct. 21, 2003

(54) ANTI PROLIFERATIVE PREPARATIONS

(75) Inventors: Etienne Soudant, Fresnes (FR); Lea Bezalel, Beer Sheva (IL); Meira Ziv, Rehovot (IL); Inon Perry, Tel Aviv (IL)

(73) Assignee: I.B.R. Israeli Biotechnology Research Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/915,768

(22) Filed: Jul. 27, 2001

(65) Prior Publication Data

US 2002/0071878 A1 Jun. 13, 2002

Related U.S. Application Data

(63) Continuation of application No. 09/367,898, filed as application No. PCT/IL98/00085 on Feb. 23, 1998, now Pat. No. 6,342,254.

(30) Foreign Application Priority Data

Feb. 23, 1997 (IL) .................................. 120291
Feb. 23, 1997 (IL) .................................. 120292
Jul. 16, 1997 (IL) .................................. 121320

(51) Int. Cl.[7] ............................................. A61K 35/78
(52) U.S. Cl. ...................... 424/753; 424/773; 424/775; 424/776; 424/725; 514/863
(58) Field of Search ................................ 424/725, 753, 424/773, 775, 776; 514/863

(56) References Cited

U.S. PATENT DOCUMENTS

| | | | |
|---|---|---|---|
| 4,309,207 A | 1/1982 | Devlin | |
| 5,104,668 A | 4/1992 | Cole et al. | |
| 5,438,073 A | 8/1995 | Saurat et al. | |
| 5,556,626 A | 9/1996 | D'Arrigo | |
| 5,738,851 A | 4/1998 | Colavito | |
| 5,994,135 A | 11/1999 | Lin et al. | |
| 6,066,781 A | 5/2000 | Sutcliff et al. | |

FOREIGN PATENT DOCUMENTS

| | | |
|---|---|---|
| JP | 2100650 | 12/1990 |
| JP | 3052820 | 3/1991 |
| JP | 6056685 | 3/1994 |

OTHER PUBLICATIONS

Suzuki et al. 1974. Clin. Pharmacol. Ther. vol. 15, No. 2, pp. 220–221.*
Dzhumasheva et al. Vestn. Akad. Nauk Kaz. SSR 1990. vol. 3, pp. 69–72.
Finamore, F. et al., "Biochemical Aspects of Morphogenesis in the Brine Shrimp, Artemia salina," *The Cell Cycle*, Ch. 12, 249–78.

Miller–Shen, J. et al., "Exceptional Seed Longevity and Robust Growth: Ancient Sacred Lotus From China," *American Journal of Botany*, 82:11, 1367–80 (1995).
Ames, B. et al., "DNA Lesions, Inducible DNA Repair, and Cell Division: Three Key Factors in Mutagenesis and Carcinogenesis," *Environmental Health Perspectives*, 101:5, 35–44 (1993).
Hayflick, L., "The Cell Biology of Aging," *Clinics in Geriatric Medicine*, 1:1, 15–27 (1985).
Samson, F., "Pharmacology of Drugs That Affect Intracellular Movement," *Intracellular Movement*, 143–158 (1976).
Pirofsky, B. et al., "Noncytotoxic Inhibition of Malignant Cell Growth by Ulex Seed Extracts," *Journal of Biological Response Modifiers*, 2:175–185 (1983).
Furusawa, E., et al., "Therapeutic Activity of Pretazettine on Rauscher Leukemia: Comparison with the Related Amaryllidaceae Alkaloids," *Experimental Chemotherapy*, 26: 36–45 (1980).
Nagainis, P. et al., "Evidence for the Presence of an Acid Protease and Protease Inhibitors in Dormant Embryos of Artemia salina," *Developmental Biology*, 68: 259–270 (1979).
Sastre, L. et al., "Purification and Properties of a Polyadenylate Polymerase from Artemia Dormant Embryos," *Biochmica et Biophysica Acta*, 661: 54–62 (1981).
Furusawa, E. et al., "Therapeutic Activity of Pretazettine, a Narcissus Alkaloid on Rauscher Leukemia: Comparison with Tazettine and Streptonigrin," *Proceedings of the Society for Experimental Biology and Medicine*, 152: 186–191 (1976).
Pirofsky, B. et al., "Ulex Seed Extracts: Lymphocyte Growth Inhibition and the Anti–H Hemagglutinins," *Vox Sang*, 42:295–303 (1982).
Ceriotti, G., "Discovery, Isolation and Physicochemical Properties of Narciclasine, a New Antimitotic of Vegetable Origin," *Tumori*, 53: 359–371, 1967.
Pettit, G. et al., "Antineoplastic Agents, 120. Pancratium Littorale," *Journal of Natural Products*, 49:6, 995–1002 (1986).
Chung, C. et al., "Pharmacological Effects of Methanolic Extract from the Root of Scutellaria baicalensis and its Flavonoids on Human Gingival Fibroblast," *Planta Med.*, 61, 150–153 (1995).

(List continued on next page.)

Primary Examiner—Christopher R. Tate
(74) Attorney, Agent, or Firm—Gary M. Nath; Todd L. Juneau; Joshua B. Goldberg

(57) ABSTRACT

A dormant preparation (DC) is provided which is capable of inhibiting proliferation of various kinds of cells. The preparation comprises an extract which is obtained from cells or tissue originating in an organism capable of entering a phase of dormancy in at least one of its parts and comprises at least one substance which induces or maintains the state of dormancy in the organism from which the cells or tissue are derived. The DC may be used for a variety of indications including human medicine and cosmetics, plant growth control and food preservation.

4 Claims, 17 Drawing Sheets

OTHER PUBLICATIONS

Staby, G. et al., "The Detection of Ethylene in the Internal Atmosphere of Bulbs," *HortScience*, 5:5, 399–400 (1970).

Staden, J., "The Levels of Endogenous Cytokinins in Daffodil Bulbs Stored under Different Environmental Conditions," *Z. Pflanzenphysiol. Bd.*, 86:323–330 (1978).

Ditre, C. et al., "Effects of α–hydroxy acids on photoaged skin: A pilot clinical, histologic, and ultrastructural study," *Journal of the American Academy of Dermatology*, 34:2, 187–195 (1996).

LeGal, Y., "Artemia salina et l'expression des messagers," *Biochimie Marine*, 175–177.

Yasuyuki, I. et al., "Sphingosine and N–methyl–sphingosine as inhibitor of cell growth," *Bibliographie et Abrégé*, 1–18 (1990).

Pirofsky, B. et al., "Noncytotoxic inhibition of malignant cell Growth by *Ulex* seed extracts," *J biol Response Mod*, 2:2, Abstract, 1983.

Pirofsky, B. et al., "*Ulex* seed extracts: lymphocyte growth inhibition and the anti–H hemagglutinins," *Vox Sang*, 42:6, Abstract, 1982.

Kosugi, K., "Cosmetic," Patent Abstracts of Japan, Pub. No. 57,102,810, Jun. 26, 1982, Application No. 55,177,865, Dec. 16, 1980.

* cited by examiner

ANTI PROLIFERATIVE PREPARATIONS

This application is a Continuation of patent application Ser. No. 09/367,898 now U.S. Pat. No. 6,342,254, filed Nov. 29, 1999 as a 371 international application PCT/IL98/00085 filed Feb. 23, 1998, the entire contents of which are hereby incorporated by reference in their entirety.

FIELD OF THE INVENTION

The present invention concerns exacts of cells or tissue or their supernatants which can inhibit proliferation of cells or tissue. The invention also provides compositions comprising such extracts as well as pharmaceutical, cosmetic and agricultural uses of the compositions and extracts.

BACKGROUND OF THE INVENTION

Dormancy is a phenomena which is found in representatives of the plant kingdom as well as the animal kingdom.

The germination of various grains and seeds comprising the necessary propagation organs is delayed under certain circumstances and yet the grains or seeds are capable of germinating after various periods of time. The period of time in which germination of such seeds may be delayed varies and depends both on intrinsic properties of the seed as well as on the nature and extremity of the environmental conditions. Seeds have been shown to be in dormancy for a few days, a year, several years and even for more than several centuries (as was discovered lately in the case of some nympheaceae and seeds of trees of the Leguminosae family (Shen-Miller, J., et al., *American Journal of Botany*, 82:1367–1380, 1995)).

In some cases, the capability to develop dormancy lies in the embryo envelopes. In such a case, the separation of the envelopes from the embryo, result in its immediate germination.

In other cases, chemical growth inhibitors capable of preventing germination are present in the embryo itself and thus even a bare embryo may remain dormant (such as in the case of Rosaceae plants such as Kerria, Peach, etc.).

In plants, a state of dormancy may be found in the whole plant or in one or more of its parts. Dormant plants are plants which have two main metabolic states in their growth cycle. In their dormant state, the plants' metabolism is extremely low, and the plant growth process is significantly inhibited although differentiation of certain cells may occur. In their active state, the plants' metabolism rate is higher, the cells divide and differentiate and there is significant growth of various parts of the plant. In some cases, the whole plant enters the dormant state. Such is the case in Narcissus plants in which during the dormant state the only remaining viable part is the bulb which is in its dormant state. In other cases, some parts of the plants may be active while other parts may be in dormancy such as, for example, is the case of apple trees.

Substances capable of inhibiting germination have also been shown to be present in the juice of fleshy fruits or in other plant organs which produce juice. Examples are tomatoes, grapes, kiwi, watermelon and grapefruit wherein pips present in the fruit do not germinate although their surroundings are suitable for germination due to the water within the fruit.

Several plant-derived substances having an effect on cell proliferation have been reported. For example, European Patent Application No. 0381514 describes compositions comprising both naturally derived as well as synthetically prepared sphingolipids which have growth inhibitory activity on various kinds of cells. Another well known plant-derived substance having an anti-mitotic effect on various kinds of human cells is the substance colchicine (Samson, F. E., *A. Rev. Pharmac. Toxic* 16:143 (1976)). The Narcissus alkaloid, pretazettine, was shown to have a cytotoxic effect on Rausher virus-carrier cells as well as anti-leukemic activity in leukemic mice although the predominant activity of the substance was shown to be an antiviral activity (Furusawa, E. et al., *Chemotherapy*, 26:36–45, (1980) and Furusawa, E. et al., *Proc. Soc. Exp. Biol. Med.*, 152:186–191, (1976)). *Ulex europaeus* seed extracts were shown to comprise a non glycoprotein lectin capable of reversibly inhibiting growth of certain lymphocytes as well as to inhibit the growth of various reticulo endothelial tumor cell lines (Pirofsky, B., et al., *Vox-Sang*, 42:295–303, (1982) and Pirofsky, B., et al., *J. Biol. Response Mod.*, 2:175–185, (1983)). Root extract of *Panex ginseng* was shown to decrease DNA synthesis measured by $[H^3]$-thymidine incorporation of V 79 Chinese hampster lung cells. Another substance, Narciclasine obtained from bulbs of various Narcissus varieties was shown, amongst other of its activities, to inhibit growth of wheat kernal radicals (Ceriotti, G., et al., *Tumors* 53:359–371 (1967)). Bulbs of *Pancratium littoral* collected in Hawaii were found to contain a product designated pancratistatin capable of inhibiting growth of various neoplastic cell lines in vitro (Pettit, G. R., et al., *J. Nat. Prod.*, 49:995–1002 (1986)).

Against this, many plant extracts having an opposite effect on cells, i.e., capable of augmenting their proliferation were also described such as, for example, the methanolic extract from the root of *Scutellaria baicalensis georgi* were shown to significantly augment the cellular activity of fibroblasts (Chung, C. P., et al., *Planta-Med*, 61:150–153, (1995)). Gibberellin-like growth substances were found in six different plant species having bulbs (Staby, G. L., *Hort. Science*, 399–400 (1970)). Several cytokinins which were found in roots that developed from Narcissus bulbs had an effect on bulb growth of the plants in which they were detected (Vanstaden, J. V., *Pflanzenphysiol.*, 86:323–30 (1978)).

The phenomena of dormancy may also be found in the animal kingdom, for example, in the small crustacean *Artemia salina* (Finamore and Clegg In: The Cell Cycle, Academic Press Ed., 249–278, 1969). The natural environment of this marine crustacea is usually briny ponds. After fertilization, the early stages of development of artemia involve the formation of a blastula which then becomes a gastrula. Under severe environmental conditions such as dehydration (drought), the gastrula is capable of forming a cyst wherein the whole organism enters a dormancy phase. The dormant artemia gastrula (commonly miscalled "artemia eggs") are capable of remaining in their dormant state for many years. When the encysted gastrula are rehydrated, the various metabolic activities of the artemia are resumed and protein synthesis can be seen after about 10 minutes. However, DNA synthesis and cell division are absent until about after 60 hours (Le Gal, Y, In: Biochimie Marine, (Ed. Masson) p. 176, 1988).

Various plant derived compositions (such as retinoic acid (U.S. Pat. No. 5,438,073) and α-hydroxy acids (Ditre, C. M., et al., *J. Am. Acad. Dermatol.*, 34:187–195, 1996)) as well as animal derived extracts have been proposed for use in the cosmetic field for stimulating the proliferation and renewal of epidermal cells. Such compositions were considered to be useful in the cosmetic field where it is accepted that the natural renewal process of epidermis is slowed down with aging. It is believed that removal of the outer surface with simultaneous stimulation of growth of new cells in the inner layers of the epidermis to divide and migrate to the outer surface, will result in skin renewal and in a younger skin appearance. However, it is also known and has been recently shown that the increase in cell division is a crucial factor in converting normal cells into premalignant or malignant cells (Ames, B. N. et al., *Environ. Health Perspect* 101:35–44 (1993)).

It is also believed today that normal human and animal cells have a finite capacity to replicate. It has been shown that the number of mitotic events that cultured normal animal cells can undergo appear to be inversely related to the age of the donor from which they were obtained (Hayflick, L., *Clin. Geriatr. Med.,* 1:15–27, (1985)). It has also been shown that cell cultures obtained from patients with accelerated aging syndromes undergo less replications than cell cultures obtained from age matched control individuals.

GLOSSARY

The following is the meaning of some terms of which will be used in the text below:

Dormancy—a state in which there is a marked decrease in the metabolic rate of cells or tissues resulting in the inhibition of growth and proliferation of the cells or tissue.

Dormans—substances naturally found in cells or tissue and which are capable of inducing cells or tissue to enter a state of dormancy or of maintaining the dormant state in cells or tissues that have already entered that state. The dormans may be obtained from a variety of plant parts which are capable of entering into a state of dormancy; from juice of various fruits which contain dormans capable of inhibiting germination of seeds within the fruit; from animals which are capable of entering a phase of dormancy in their life cycle, e.g. gastrula of certain crustaceans such as artemia or dafnia: etc. In some cases, the dormans are found within a dormant tissue, e.g. in a dormant seed or in the gastrula of artemia or dafnia; in other cases the dormans are found in a tissue surrounding the dorman tissue or organ, e.g. in a fruit juice surrounding a dormant seed.

Extract—At least one substance obtained by any of a variety of extraction methods known in the art. For example, the extract may be an aqueous extract, a glycolic extract an alcoholic extract, an oily extract, etc. The extract in accordance with the invention is obtained from cells or tissues from a part of a plant or animal capable of entering a state of dormancy. The cells or tissue may be obtained directly from the plant or animal and the extract may then be prepared therefrom. Alternatively, cell cultures may first be prepared from the plant or animal cells or tissues and then the cell cultures may be grown for various periods of time. In order to prepare an extract, the cells are then harvested from the cell cultures, the cells and their growth medium are separated and an extract may be prepared either from the cells themselves or from the growth medium (which will be referred to as "supernatant") which contains substances secreted by the cells into their growth medium. Thus, the "extract" may be obtained directly from plant or animal tissue or from an animal or plant cell or tissue culture.

Dorman extract—an extract obtained from a plant cell or tissue, from fruit or from an animal cell or tissue which comprises dormans.

Enriched dorman preparation (EDP)—a preparation derived from a natural source which comprises dormans in a concentration larger than that which is found in a natural unprocessed extract. The EDP may be obtained by purification of a natural extract to obtain fractions which contained dormans in the larger concentration, e.g. by various chromatographic techniques, by filtration, etc., as well as by biological means including growing cells or tissue which are capable of producing dormans under conditions in which they produce dormans in relatively large quantities and collecting their secretion products. In order to determine whether a preparation is an enriched dorman preparation, the preparation may be assayed for a specific biological activity associated with dormans, as described below. EDP contains a substantially higher concentration of dormans as compared to the natural preparation, e.g. at least 1.5 folds, preferably 2 folds and typically at least 2.5 folds to the concentration of the dormans in the natural preparation.

Producer cells or producer tissue—cells or tissue which are capable of producing dormans which may thus be extracted therefrom.

Target cells or target tissue—cells or tissue which are contacted with dormans, in accordance with the invention and which thereby enter a state of inhibition of their growth or proliferation or maintain such a state as the result of contact with dormans.

Dorman analog—a substance, typically synthetic, which has a dorman-like activity in that it is capable of inducing dormancy in the same cells or tissue induced to dormancy by the dorman and which, in accordance with the invention, is also capable of inhibiting growth and proliferatin of target cells or tissue.

Dorman composition (DC)—a composition comprising, as active ingredient, an amount of dorman (e.g. as a dorman extract) or dorman analog effective in inhibiting growth and proliferation of target cells or tissue ("effective amount"). A dorman composition may comprise a naturally derived EDP, a composition comprising synthetic dormans as well as dorman analogs.

Active Extract (AE)—extracts obtained from cells or tissues from a part of a plant or animal capable of entering a state of dormancy during the non dormant state.

SUMMARY OF THE INVENTION

In accordance with the invention, use is made of a dorman composition. The composition may be used for inhibiting proliferation of cells, particularly cells xenogeneic to the producer cells or tissue. By one preferred embodiment of the invention, the compositions are used in human medicine and cosmetics. In accordance with another embodiment, the compositions are used for controlling plant growth. By yet a further embodiment, the compositions of the invention are used in food preservation.

By one aspect of the invention there is thus provided a preparation capable of inhibiting proliferation of target cells or target tissues, comprising a member selected from the group consiting of:

(i) an extract obtained from producer cells or producer tissue, said cells or tissue originating in an organism capable of entering a phase of dormancy in at least one of its parts, said extract comprising at least one substance which induces or maintains said state of dormancy in an organism from which said producer cells or tissues are derived, (ii) a dormancy inducing fraction of said extract; and (iii) a dormancy inducing substance derived from said extract or fraction.

By one embodiment the composition comprises an enriched dorman preparation (EDP) which, as defined above, comprises dormans in a concentration larger than that which is found in a natural unprocessed extract.

The producer cells or tissues from which the extract is obtained may be of the same origin as said target cells or tissues but are preferably of a different origin. In accordance with one embodiment of the invention, said target cells or tissue are human cells or tissue and said producer cells or tissue are plant or non human animal cells or tissue. In accordance with another embodiment of the invention, said target cells or tissue are plant cells or tissue.

In accordance with one preferred embodiment of the invention, the dorman composition is a pharmaceutical or cosmetic composition for inhibiting cell proliferation within the body. In accordance with another embodiment of the invention, said composition is used for inhibiting germination of seeds (being either natural or artificially prepared) or growth of seedlings for the purpose of maintaining seedlings in a dormant state for example during storage. In accordance with a further embodiment of the invention, the dorman composition is used in fresh food preservation.

By one embodiment, the dormans or the extracts used in accordance with the invention are derived from dormant plants.

Compositions in accordance with the invention obtained from bulbs of dormant plants while in their dormant state are capable of inhibiting the growth of seedlings as well as to inhibit the proliferation of various target cells, including various mammalian cells, e.g. human cells, to a significantly higher extent than preparations obtained under the same conditions from bulbs of the same plant being in their active state. It was also found that dorman compositions obtained from cell cultures prepared from various parts of dormant plants and induced into dormancy are also capable of inhibiting the growth of seedlings as well as to inhibit the proliferation of various cells, including various mammalian cells, e.g. human cells. These DCs, in a wide range of concentrations, had no noticeable toxic effect on the target cells, this being in contrast to most substances which have an anti-proliferating effect.

In accordance with the invention, any plant capable of entering a dormant state may be used for obtaining an DC. Some non-limiting examples of such plants, as well as the parts of such plants which enter a dormant state (designated "D-part") and from which the DC may be obtained, are shown in the following Tables I and II:

TABLE I (Bulbs, corms, roots, rhizomes)

| Name | Family | D-part |
| --- | --- | --- |
| Allium | Liliacease | bulbs |
| Amaryllis belladona | Amaryllidacea | bulbs |
| Anemone | Ranunculacea | perennials & tuberous or fibrous roots |
| Babiana | Iridacca | corms |
| Brodiaea | Liliaceae | corms |
| Chionodoxa | Liliaceae | bulbs |
| Crocus | Iridacea | corms |
| Ornithogallum | Liliaceae | bulbs |
| Cyclamen | Primulaceae | perennials & tuberous roots |
| Endymion | Liliaceae | bulbs |
| Arum | Araceae | perennials & Tuberous roots |
| Freesia | Iridacea | corms |
| Fritillaria | Liliaceae | bulbs |
| Galanthus | Amaryllidacea | bulbs |
| Hippeastrum | Amaryllidacea | bulbs |
| Hyancinthus | Liliaceae | bulbs |

TABLE I-continued (Bulbs, corms, roots, rhizomes)

| Name | Family | D-part |
| --- | --- | --- |
| Leek | Liliaceae | bulbs |
| Ipheion uniflorum | Amaryllidacea | bulbs |
| Iris | Iridacea | bulbs & rhizomes |
| Ixia | Iridacea | corms |
| Leucojum | Amaryllidacea | bulbs |
| Lilium | Liliaceae | bulbs |
| Muscari | Liliaceae | bulbs |
| Narcissus | Amaryllidacea | bulbs |
| Oxalis | Oxalidaceae | bulbs & rhizomes |
| Paeonia | Paeoniaceae | tuberous perennials |
| Puschkinia scilloides | Liliaceae | bulbs |
| Ranuculus | Ranunculacea | tubers or perennials |
| Radohypoxis | Hypoxidaceae | bulbs |
| Rhodophiala | Amaryllidacea | bulbs |
| Scilia | Liliaceae | bulbs |
| Sparaxis | Iridacea | corms |
| Raritimum | Liliaceae | bulbs |
| Triteleia | Amaryllidacea | corms |
| Tulipa | Liliaceae | bulbs |
| Tritonia crocata | Iridacea | corms |
| Watsonia pyramidata | Iridacea | corms |
| Zantedeschia | Araceae | rhizomes |
| Begonia | Begoniceae | rhizomes |
| Caladium | Araceae | perennials & tuberous roots |
| Canna | Cannaceae | perennials & tuberous roots |
| Crocosmia | Iridacea | corms |
| Dahlia | Asteraceae | perennials & tuberous roots |
| Gladiolus | Iridacea | corms |
| Gloriosa rothschildiana | Liliaceae | perennials & tuberous roots |
| Homeria collina | Iridacea | corms |
| Hymenocallis | Amaryllidacea | bulbs |
| Liatris | Asteraceae | perennials |
| Polianthes tuberosa | Agavaceae | perennials & tuberous roots |
| Tigridia pavonia | Iridacea | bulbs |
| Zantedeschia | Araceae | rhizomes |
| Zephyranthes | Amaryllidacea | bulbs |
| Colchicum | Liliaceae | corms |
| Lycoris | Amaryllidacea | bulbs |
| Sterenbergia lutea | Amaryllidacea | bulbs |
| Pancratium | Liliaceae | bulbs |

TABLE II (Deciduous fruit trees, shrubs, seeds)

| Name | Family | D-part |
| --- | --- | --- |
| Malus - crabapple | Malus | Deciduous & fruit trees & shrubs |
| Mangifera | Anacardiaceae | Deciduous & fruit trees & shrubs |
| Peach | Rosaceae | Deciduous & fruit trees & shrubs |
| Persimmon | Ebenaceae | Deciduous & fruit trees & shrubs |
| Pistacia chinensis | Anacardiaceae | Deciduous & fruit trees & shrubs |
| Prunus | Rosaceae | Deciduous & fruit trees & shrubs |
| Fraxinus | Oleaceae | Deciduous & fruit trees & shrubs |
| Pyrus | Rosaceae | Deciduous & fruit trees & shrubs |
| Quercus | Fagaceae | Deciduous & fruit trees & shrubs |

TABLE II-continued (Deciduous fruit trees, shrubs, seeds)

| Name | Family | D-part |
| --- | --- | --- |
| Salix | Salicaceae | Deciduous & fruit trees & shrubs |
| Actinidia | Actinidiaceae | Deciduous & fruit trees & shrubs |
| Akebia quinata | Lardizabalaceae | Deciduous & fruit trees & shrubs |
| Blueberry | Vitaceae | Deciduous & fruit trees & shrubs |
| Apple | Rosaceae | Deciduous & fruit trees & shrubs |
| Aloysia | Verbenaceae | Deciduous & fruit trees & shrubs |
| Campsis | Bignoniaceae | Deciduous & fruit trees & shrubs |
| Celastrus | Celastraceae | Deciduous & fruit trees & shrubs |
| Cellery | Apiaceae | seeds |
| Clematis | Ranunculaceae | Deciduous & fruit trees & shrubs |
| Grape | Vitaceae | Deciduous & fruit trees & shrubs |
| Humulus | Cannabaceae | Deciduous & fruit trees & shrubs |
| Fig | Moraceae | Deciduous & fruit trees & shrubs |
| Wisteria | Fabaceae | Deciduous & fruit trees & shrubs |
| Bean | Fabaceae | Deciduous & fruit trees & shrubs |
| Lathyrus pea | Fabaceae | Deciduous & fruit trees & shrubs |
| Tropaeolum | Tropaeolaceae | Deciduous & fruit trees & shrubs |
| Amelanchier | Rosaceae | Deciduous & fruit trees & shrubs |
| Cotoneaster | Rosaceae | Deciduous & fruit trees & shrubs |
| Barberry | Berberadaceae | Deciduous & fruit trees & shrubs |
| Enkianthus | Ericaeae | Deciduous & fruit trees & shrubs |
| Eunymus | Celastraceae | Deciduous & fruit trees & shrubs |
| Kerria japonica | Rosaceae | Dedicuous & fruit trees & shrubs |
| Parsnip | Apiaceae | seeds |
| Passiflora | Passifloraceae | Deciduous & fruit trees & shrubs |
| Rhdodendron | Ericaeae | Deciduous & fruit trees & shrubs |
| Acacia | Fabaceae | Deciduous & fruit trees & shrubs |
| Albizia | Fabaceae | Deciduous & fruit trees & shrubs |
| Almond | Rosaceae | Deciduous & fruit trees & shrubs |
| Ampelopsis | Vitaceae | veciduous & fruit trees & shrubs |
| Anethum | Apiaceae | seeds |
| Annona cherimola | Annonaceae | Deciduous & fruit trees & shrubs |
| Apricot | Rosaceae | Deciduous & fruit trees & shrubs |
| Artemisia | Asteraceae | Deciduous & fruit trees & shrubs |
| Asparagus | Liliaceae | seeds |
| Blackberry | Rosaceae | Deciduous & fruit trees & shrubs |
| Carrot | Apiaceae | seeds |
| Carya pecan | Juglandeaceae | Deciduous & fruit trees & shrubs |
| Cherry | Rosaceae | Deciduous & fruit trees & shrubs |
| Corn | Poaceae | seeds |
| Helianthus | Asteraceae | seeds |
| Cucumber | Cucurbitaceae | seeds |
| Filbert | Betulaceae | Deciduous & fruit trees & shrubs |
| Gooseberry | Saxifragaceae | Deciduous & fruit trees & shrubs |
| Gourd | Cucurbitaceae | Deciduous & fruit trees & shrubs |
| Lettuce | Asteraceae | seeds |
| Melon | Cucurbitaceae | seeds |
| Okra | Malvaceae | seeds |
| Onion | Amaryllidaceae | seeds or bulbs |
| Peanut | Fabaceae | seeds |
| Pear | Rosaceae | Deciduous & fruit trees & shrubs |
| Pumpkin | Cucurbitaceae | seeds |
| Punika garantium | Punicaceae | seeds |
| Radish | Cruciferae | seeds |
| Walnut | Juglandeaceae | Deciduous & fruit trees & shrubs |
| Ziziphus jujuba | Rhamanceae | Deciduous & fruit trees & shrubs |
| Raspberry | Rosaceae | Deciduous & fruit trees & shrubs |
| Strawberry | Rosaceae | Deciduous & fruit trees & shrubs |
| Turnip & rutabaga | Cruciferae | Deciduous & fruit trees & shrubs |
| Malva | Malvaceae | seeds |
| Verbascum | Scrophulariaceae | seeds |
| Chenopodium | Chenopodiaceae | seeds |
| Nelumbo | Nelumbonaceae | seeds |
| Lupinus | Papilonaceaee | seeds |

In accordance with the invention, DC is preferably obtained from plants which are in their dormant state either as a result of the natural process of dormancy or as a result of being externally induced into dormancy by exposure which induce a dormant state e.g. conditions as incubation at a dormancy inducing temperature for a sufficient period of time. The conditions for inducing dormancy in various dormant plants may vary (e.g. the incubation temperature and the duration of the incubation) and are known to a person versed in the art. Thus for example there are plants (such as Narcissus) induced into dormancy by their exposure to relatively high temperatures. Against this, other plants (such as tulip) will be induced into dormancy by their exposure to relatively low temperatures. Other factors such as light, humidity, concentration of various growth factors, etc. may also be used to induce dormancy.

In accordance with one preferred embodiment of the invention, the DC is obtained from a part of the plant capable of entering dormancy (D-part), e.g. from bulbs. Bulbs induced into their dormant state may either be used immediately for the preparation of DC or, alternatively, may be stored under conditions which maintain a dormant state, e.g. in the case of Narcissus these include high temperature and low humidity. In addition to bulbs, other parts of dormant plants such as combs, roots, seeds, etc., may also be induced into dormancy as explained above and then used for obtaining DC therefrom.

In accordance with another embodiment of the invention, the dorman extract is obtained from cell cultures which were prepared from any part of a dormant plant (e.g. bulbs) and induced into dormancy. The culture may be obtained by inoculation of bulbs of dormant plants having inflorescence stalk initials into a suitable medium to form callous cultures of the bulb extracts. The cell cultures are then typically grown to confluency and very small bulb parts are formed in the cell culture (termed "bulblets"). Induction of a dormant state in the cell cultures or bulblets is obtained by their exposure to conditions which induce dormancy conditions, such as incubation at a dormancy inducing temperature for a sufficient period of time. Dormancy may also be induced in vitro by exposing the cell cultures or bulblets to various types of chemical stresses (low or high concentrations of sugar, salts, etc.).

In addition to bulblets, cell cultures derived from other parts of dormant plants such as combs, roots, seeds, etc., may also be used for obtaining cell culture derived dorman extracts.

By yet another embodiment, the dorman analogs of the invention may be synthetically prepared by any one of the methods known in the art such as by recombinant DNA techniques, chemical synthesis, combinational chemistry, etc., the dorman analogs maintaining substantially similar characteristics as far as their ability to induce dormancy and inhibit proliferation of target cells of the dormans on which they are based.

Preferably, a plant derived DC of the invention is obtained as an aqueous extract of the plant material. The aqueous extract may be prepared by homogenizing the plant material and then suspending the homogenate in an aqueous solution. However, non aqueous plant extracts obtained by any one of the extraction methods known per se, may also at times be used in accordance with the invention.

In accordance with a further embodiment of the invention, the EDPs are obtained from juice of fruits or other juice producing plant organs. Fruits typically contain dormans which inhibit germination of the seeds and pips while these are within the fruit. Examples of juices from which dormans may be purified are juice of citrus fruits, grapes, tomato, kiwi, etc. The fruit juice may be used as such or alternatively, the dormans can be purified from the fruit juice as explained below.

In accordance with yet another embodiment of the invention, the dormans are extracted from producer cells originating from animals capable of entering a dormant phase during their life cycle. During the dormant phase, the animals' metabolic rate is lowered to a minimum and there is an arrest in cell proliferation. Examples of such animals are various marine crustacea such as artemia, dafnia and cyclops.

As explained above with regards to plant derived DC, animal derived DC may also be obtained from animals which are in their dormant state as a result of the natural process of dormancy or as a result of being externally induced into dormancy by exposure to dormancy-inducing conditions such as dehydration (*Artemia salina*) or anoxia (*Artemia franciscana*). The dormans may be extracted from the animal tissue by various methods known per se.

The animal derived DC may be obtained from the animals or their organs as such. Alternatively, cell cultures may first be prepared from the dormant animal, and after maintaining the cells in culture for various periods of time, DC may then be extracted either from the supernatant or by harvesting the cells and/or extracting the DC therefrom.

The DC of the invention may be purified from the producer cells by a variety of methods known per se, for example by chromatography (e.g. TLC, HPLC, ion exchange) by size fractionation (e.g. dialysis, gel filtration), etc.

In accordance with the invention, it has been realized for the first time that, when administered to an individual, the anti-proliferative activity of said dorman composition may slow down the cell division rate of the cells present in the inner layers of the epidermis.

Another aspect of the invention is thus the use of said dorman compositions as a cosmetic or dermatological composition useful for the maintenance of the juvenile appearance of an individual's skin or for the treatment of age related skin changes.

In accordance with this latter aspect of the present invention, a dermatological or cosmetic composition is provided comprising from about 0.0001%, preferably from about 0.001%, typically from about 0.01% up to about 5% preferably up to about 1% by weight of dorman extract or dorman analog together with a dermatologically or cosmetically acceptable carrier.

The dermatological or cosmetic compositions of the invention may be administered in various forms such as in the form of a balm, an emulsified gel, an aqueous-alcoholic gel, anhydrous gel, an oil in water (O/W) type emulsion, a clear gel, cream containing liposomes, etc.

The cosmetic or dermatological compositions are typically topically administered. However, it may at times be advantageous to administer the compositions by other administration modes, such as, for example, by subcutane injections, by orally administered capsules or by iontophoresis (which involves the use of electric fields to increase the penetration of ionic active substances).

Due to their significant anti proliferative effect said dorman compositions may also be used for the treatment of various malignancies. As mentioned above, the cell division rate is a significant factor in determining the probability of a cell to become a premalignant or malignant cell. In addition, as known, the formation of a benign or malignant tumor is dependent, inter alia, on continuous divisions of the cells forming the tumor. Administration of the dorman compositions to an individual before the formation or at early stages of the formation of a benign or malignant tumor may result in the delay or prevention of the formation of a fully fledged tumor in the treated individual. Administration of said extracts to an individual suffering from a fully fledged benign or malignant tumor may result in the reduction of the tumor load in the treated individual and in the alleviation of the tumor-related symptoms. Said dorman compositions may be effective in the treatment of primary as well as secondary (metastatic) tumors. Said extracts may also be administered in combination with one or more known anti-tumorigenic treatments (e.g. chemotherapeutic agents, radiation etc.) to achieve a synergistic anti-tumorigenic effect. The doses of said extracts to be administered to an individual as well as the treatment modality will be dependent on characteristics of the treated individual (age, weight, medical history, etc.) as well as on characteristics of the developing or existing tumor (benign or malignant, size, origin, primary or secondary, etc.). In individuals having a high risk of developing a primary or secondary tumor, the dorman compositions may be administered routinely in order to reduce the probability of tumor formation.

The present invention thus further provides a composition comprising a dorman extract capable of inhibiting the proliferation of cells, for the administration to an individual having a benign or malignant tumor or being at a high risk of developing a tumor.

By yet an additional aspect of the invention, dorman compositions may be used to enhance the therapeutic index of chemotherapeutic and radiation treatments. In an individual receiving such treatments, normal dividing cells such as cells of the inner lining of the intestines, cells of hair follicles and hematopoietic cells are also harmed by the chemotherapeutic agents or radiation which are aimed at destroying the malignant cells of which a large percent are dividing cells. By administration of dorman compositions to an individual prior to or together with such treatments, it may be possible to inhibit the proliferation of a significant percent of the normal cells. As a result, toxic side effects due to the influence of the treatments on normal cells may be significantly reduced and when beneficial, higher concentrations of the chemotherapeutic or radiation treatments may be used. In order to facilitate the toxicity reducing affect of the dorman composition, it may at times be administered directly to a needing site, tissue or organ, e.g. onto the skin.

The present invention thus provides by a further of its aspects, a composition capable of inhibiting the proliferation of cells, for administration to an individual receiving chemotherapeutic or radiation treatments, comprising an effective amount of dorman, dorman extract or dorman analog.

Other therapeutic applications of the dorman compositions include inhibition of fibrosis, e.g. skin fibrosis, cirrhosis, and others. It should be noted that hitherto, fibrosis, which is an over proliferation of fibroblasts, has been treated by cytotoxic drugs, but with a limited application due to their general non specific toxicity. Inhibition of the fibroblast proliferation by the use of the dorman composition of the invention, provides a viable, less toxic alternative. In a similar manner, the dorman compositions of the invention may also be useful in the treatment of psoriasis which results from over proliferation of keratinocytes. Seborrheic keratosis, papilomas and warts may also be treated by the dorman compositions.

Another possible application of the dorman composition of the invention is in preservation of organs or tissue prior to their use for transplantation.

Other applications of said dorman compositions may be, for example, in the treatment of scalp baldness (Alopecia) which is many times one of the phenomenas associated with aging of the skin in an individual. In individuals suffering from Alopecia, the life span of scalp hair decreases substantially (e.g. from a life span of about 3 years in a normal individual to a life span of about one year in an individual suffering from Alopecia). Therefore, decreasing the rate of hair growth in an individual having a high probability of developing Alopecia or in an individual already showing for signs of scalp hair loss, will decrease the extent of such hair loss. Administration of the dorman compositions of the invention to such an individual may result in a partial or complete decrease of the hair loss. For this purpose, the dorman comprising compositions may be administered either topically at the site of scalp hair loss or, alternatively, in other cases may be administered systemically.

An additional phenomena which may be treated by administration of the dorman comprising compositions of the invention is associated with overgrowth of hair in various parts of an individual's body, such as arms, back, etc. (Hirsutism). Such undesired overgrowth of hair appears many times in aging individuals and, at times, is associated with loss of scalp hair in the same individual. Due to their ability to reduce cell growth, compositions of the invention may be useful in reducing such undesired overgrowth of hair.

The amount of the dorman comprising compositions to be administered for the above two indications, the administration regimes as well as their mode of application will again depend both on characteristics of the treated individual (age, size, gender, etc.) as well as on parameters associated with the phenomena to be treated (such as the extent of scalp hair loss, the specific body parts in which there is overgrowth of hair, etc.).

In addition, the dorman composition may be useful as a complementary agent administered in combination with or following hair removal treatments such as, for example, shaving (where said extract may be incorporated in an aftershave solution) or hair stripping (e.g. by wax).

Another application of the dorman composition may involve its administration to an individual during the period in which a scar is formed, e.g. after an operation in order to decrease scar formation. By slowing down the rate of the healing process in such an individual, the final scar may be much less apparent. In addition, the anti-fibrotic effect of the dorman compositions decreases the formation of cheloids which commonly appear after healing.

The dorman composition may also be useful for extending the duration of a tan in an individual. Following exposure to the sun, epidermal cells comprise a high concentration of melanin. During skin renewal such melanin comprising cells are shed. By slowing down the cell renewal process in the skin, the dorman composition causes the melanin comprising cells and thus the tan to remain for a longer period of time.

In addition to inhibiting proliferation of various cells, said dorman compositions are also capable of slowing seed germination and inhibiting growth of various plant seedlings. Following germination of seeds, roots and hypocotyls begin to develop in the seedling. Incubation of the plant seedlings with the dorman composition results in the inhibition of the elongation of the seedling roots and hypocotyls. The dorman compositions may therefore be used for weed control, wherein their administration at an appropriate concentration may result in the inhibition of growth of non desirable weeds while not affecting the growth of the desired plant. In view of the natural origin of the dormans, their administration has no noticeable toxic effect on cells or tissue on which they are induced to act or on the environment. In addition, at times it may be useful to use such compositions for long term storage of seeds and seedlings.

The present invention thus provides a dorman composition having the activity of slowing and inhibiting the growth of plant seeds and/or seedlings comprising said dorman extract.

A further application of the dorman composition of the invention is in the preservation of fresh produce, e.g. vegetables, fresh fish eggs, fish shells, etc.

The invention also provides a process for the preparation of an anti-proliferative composition comprising mixing dormans or DC with a carrier so as to yield an anti-proliferative composition with an anti-proliferative effective amount of dormans in said composition. Such a prepared composition may be used, depending on the nature of the carrier, in therapy, cosmetics, food preservation or agriculture. Such a process for preparing a pharmaceutical or cosmetic composition typically comprises preparing an DC, and mixing it with an appropriate pharmaceutical or cosmetic acceptable carrier, the amount of DC being such so as to yield a final therapeutically or cosmetically (as the case may be) effective amount of dormans in the composition. Also provided is use of dormans or an DC for the preparation of such a pharmaceutical or cosmetic composition.

As will be appreciated, the various applications of the dorman composition of the invention given above, are examples of a myriad of possible applications of these compositions, all having in common the inhibition of proliferation of target cells.

In the following, the invention will be illustrated by some non-limiting examples with occasional reference to the figures.

BRIEF DESCRIPTION OF THE FIGURES

FIG. 2 is a histogram showing the number of fibroblasts in a microculture at different periods of time after their incubation with various concentrations of the following:

Figure 1A:
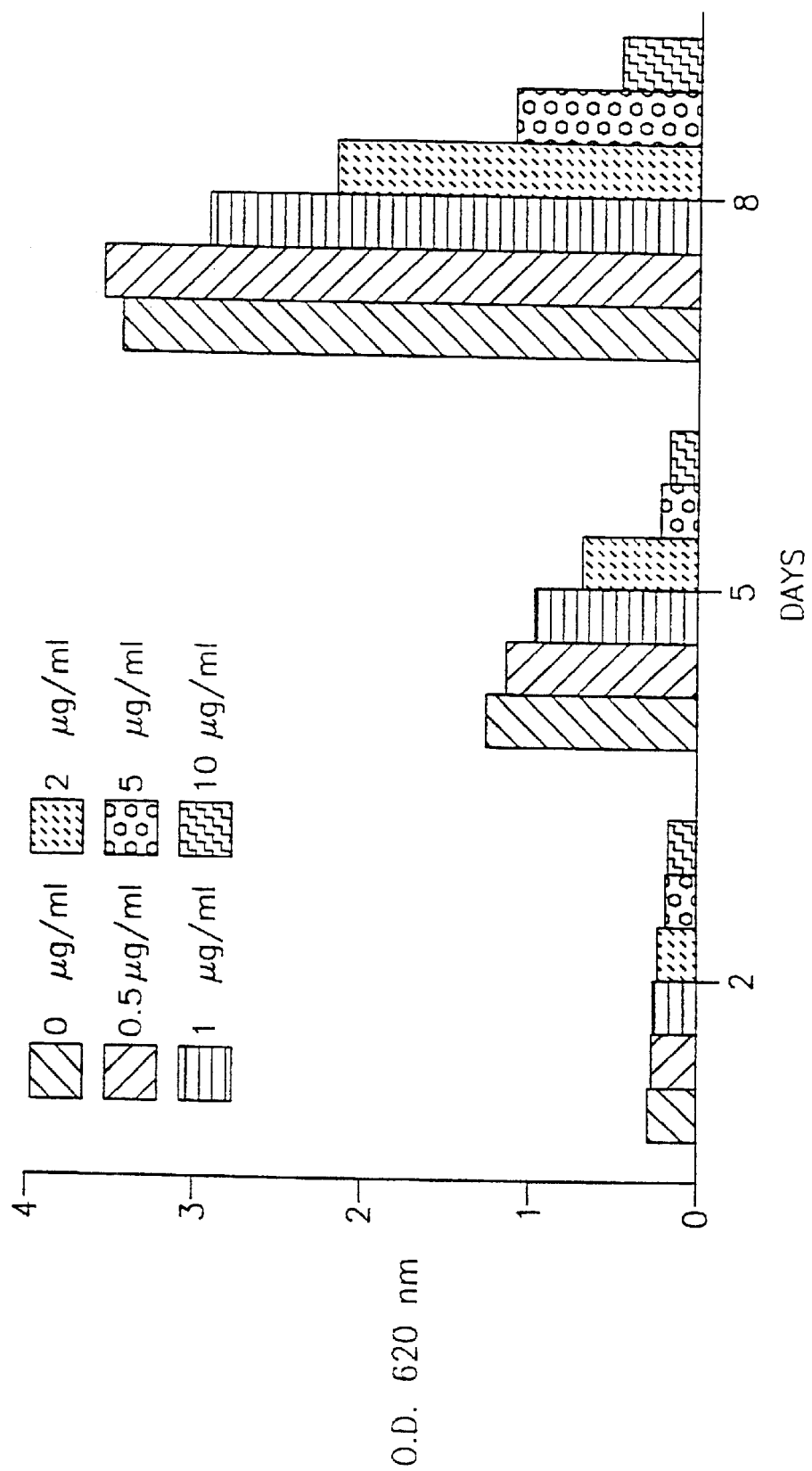
FIG. 1 is a histogram showing the number of keratinocytes in a cell culture well at different periods of time after their incubation with various concentrations of the DC IBR-1 (obtained from a dormant plant (FIG. 1A) or the AE IBR-3 (obtained from an active plant) (FIG. 1B). As a control, the cells were incubated with growth medium alone (0 µg/ml of the tested DC or AE). The number of cells in each well was determined by the microculture methylene blue assay (described in Example II) and the dyed culture plates were read at 620 nm.

Group A shows the effect of a cream containing 5% IBR-1 on the elongation of the duration of a tan 5 days after administration of the creams.

Group B shows the same effect as Group A 17 days after administration of the creams.

Group C shows the effect on the duration of the tan (shortening) of a cream comprising alpha hydroxy acid (AHA) as compared to the tan without cream 5 days after administration of the creams.

Group D shows the same effect as Group C 17 days after administration of the cream.

EXAMPLES

Example I

A: Effect of Narcissus Bulb DC Prepared From Narcissus Field Bulbs on Growth of Cucumber Seedlings (a) Inducing Dormancy in Narcissus Field Bulbs Narcissus field bulbs were obtained and subjected to hot water having a temperature of 45° C. for 2–4 hours. The bulbs were then either used immediately for the preparation of water soluble extracts or, alternatively, maintained in a dry room at a temperature of 30° C. for a maximal period of 8 months after which they were used for the preparation of the plant extract.

(b) Preparation of Extracts From Narcissus Bulbs

Active or dormant Narcissus field bulbs (induced into dormancy as explained above) were disinfected in soap water for a period of 1 hour. The bulbs were then cut and homogenized in distilled water (30 sec×3) using a Homogenizer Ultra-Turbo-turax. The homogenized preparation of the bulbs was then filtrated through a first 0.45 m sterile filter and then through a second 0.22 µm filter and the preparation which was not maintained on the filters was then collected. The concentration is defined as weight of original bulb (gr.) per final extract volume (ml).

(c) The Effect of the Narcissus Field Bulb Extracts on Growth of Cucumber Seedlings (i) Experimental assay:

Cucumber seeds cv. *"Delila"*, 1994–1995, 95% germination, 99.9% purity were germinated in tap water and then incubated in the dark at 27° C. for about 20 hours until root initiation (1–2 mm). Each experimental group comprised Petri dishes which were filled each with 2 mls of DC (IBR-1) originated from dormant Narcissus field bulbs obtained as explained above in various concentrations. One layer of filter paper was placed in each of the petri dishes and 10 cucumber seeds, germinated as explained above, were placed on the paper. The petri dishes were incubated for 24 to 72 hours at 26° C. to 28° C. in the dark.

The effect of the tested bulb extracts in various concentrations were tested on two parameters of the cucumber seeds:

1. Root elongation
2. Hypocotyl elongation.

These two parameters were tested every 24 hours after the incubation of the seeds with the tested extract and every 24 hours after that.

(ii) Results:

As seen in Table 3 below, DC IBR-1 showed sufficient inhibitive activity on the seedlings' growth, as measured by the length of the roots and hypocotyls of seeds which were incubated with DC IBR-1compared to the length of the same organs incubated with sterile water. The inhibitive activity of DC IBR-1 was dose dependent.

TABLE 3

Growth of seeds with and without extract:

| Extract source | 24 hrs | | 48 hrs | |
| --- | --- | --- | --- | --- |
| | Root (mm) | Hypocotyl (mm) | Root (mm) | Hypocotyl (mm) |
| Sterile Water | 30 | 2 | 47 | 7 |
| DC from Narcissus | | | | |
| 0.2 gr./ml | 4 | 0 | 4 | 1 |
| 0.1 gr./ml | 5 | 0 | 5 | 2 |
| 0.05 gr./ml | 6 | 0.5 | 10 | 2 |
| 0.01 gr./ml | 16 | 1 | 26 | 4 |
| 0.005 gr./ml | 22 | 2 | 35 | 7 |
| 0.001 gr./ml | 25 | 2 | 41 | 7 |

Inhibition (%) of seed growth by extracts:

| Extract source | 24 hrs (% inhibition) | | 48 hrs (% inhibition) | |
| --- | --- | --- | --- | --- |
| | Root | Hypocotyl | Root | Hypocotyl |
| Sterile Water | 0 | 0 | 0 | 0 |
| DC from Narcissus | | | | |
| 0.2 gr./ml | 87 | 100 | 91 | 86 |
| 0.1 gr./ml | 83 | 100 | 89 | 71 |
| 0.05 gr./ml | 80 | 75 | 79 | 71 |
| 0.01 gr./ml | 47 | 50 | 45 | 43 |
| 0.005 gr./ml | 27 | 0 | 25 | 0 |
| 0.001 gr./ml | 17 | 0 | 13 | 0 |

Example I
B: Reversibility of the Effect of Narcissus DC on Growth of Cucumber Seedlings (i) Experimental Assay:

(a) The experiment was conducted in an identical manner to that described in I(A) above. The effect of the DC on growth of roots and hypocotyls of cucumber seeds was measured 24 and 72 hours after incubation. 72 hours after incubation, the seeds were washed with sterile distilled water and incubated with sterile distilled water for an additional 72 hours at 27° C. in the dark. The length of the roots and hypocotyls of the seeds was measured again 144 hours after the beginning of incubation (72 hours after washing away the DC).

(ii) Results:

As seen in Table 4 below, after washing away the Narcissus derived DC which had an inhibitive effect on the growth of roots and hypocotyls of cucumber seeds, the roots and hypocotyls began to grow again. Thus, the inhibitive effect of DC was reversible and non toxic. The same effect was apparent at lower concentrations of the DC incubated with the seeds as well (results not shown).

TABLE 4

| Time Extract | 24 H | | 72 H | | 144 H (72 Hours after washing) | |
| --- | --- | --- | --- | --- | --- | --- |
| | Root (mm) | Hyptocotyl (mm) | Root (mm) | Hyptoctyl (mm) | Root (mm) | Hypocotyl (mm) |
| Sterile water | 44.9 | 6.5 | 111.7 | 17.5 | — | — |
| DC 0.2 gr/ml | 2.6 | 1.5 | 2.7 | 6.2 | 43.3 | 22.9 |

Example II
Effect of Narcissus Bulb Derived DC on Proliferation of keratinocytes (a) Preparation of Keratinocyte Cultures Human keratinocyte cultures were prepared as described in Ben Bassat H., et al., *Plastic and Reconstructive Surgery*, 89:511, (1992). Generally keratinocyte cultures were initiated from small biopsy specimens (about 1 $cm^2$) of split-thickness skin. The biopsy specimens from healthy donors were obtained under local anesthesia with 1% lidocaine. The biopsy was incubated in trypsin-EDTA at 4° C. for 18–20 hours. Thereafter, the epidermis was separated and the epithelium desegregated in trypsin-EDTA to form a single cell suspension. Trypsin 0.125%-EDTA 0.025% in Puck's saline with ×10 antibiotics, 1000 U/ml penicillin, 1000 μg/ml streptomycin, 0.0025 μg/ml amphotericin B and 0.4 mg/ml gentamycin were used for these procedures. Trypsin solutions were prepared from trypsin 1:250 strength.

The cell suspensions prepared as described above, were inoculated at a concentration of $3-6 \times 10^6$ cells into 25 $cm^2$ Falcon flasks which were pre-prepared to contain $2 \times 10^5$ lethally irradiated 3T3 mouse fibroblasts as a feeder layer.

The flasks were incubated at 37° C. 10% $CO_2$ for about 8–10 days until the cultures were about 80% confluent. At this stage, the cells in each flask were released by addition of trypsin 0.25%-EDTA 0.05% (1:1) without antibiotics and the released cells after being washed were inoculated into 96-well microplate at a concentration of $3 \times 10^4$ cells per well without feeder layers in keratinocyte medium (Kmed) according to Rheinwald and Green (Rheinwald T. G. and Green, H., *Nature*, 265:421–424 (1988)) to form a secondary culture.

(b) Effect of Narcissus Bulb Derived DC on the Proliferation of Keratinocytes (i) Experimental assay:

Narcissus bulb extracts were obtained as described in Example I(b) above from active and dormant bulbs. The secondary keratinocyte cell cultures seeded in microplates as described above, were further grown in Kmed for a period of 3–4 days. The microplates were then divided into the following main groups:

(1) keratinocytes which were continuously grown in Kmed;

(2) keratinocytes grown in Kmed containing the AE IBR-3 prepared from active Narcissus bulbs in several concentrations (from 0.5 μg/ml-10 μg/ml, each concentration forming a separate experimental group) and (3) keratinocytes grown in Kmed medium comprising the DC IBR-1 obtained from dormant Narcissus bulbs at various concentrations (0.5 μg/ml-10 μg/ml each concentration forming a separate experimental group).

Each experimental group contained 5 wells. The growth medium containing DC IBR-1 or AE IBR-3 was changed every 24 hours for a period of 5 days after which the medium was removed from all of the wells and fresh Kmed medium without any plant extract was added and the cultures were grown in it for an additional 3 days.

The effect of the tested DC or AE on the proliferation of the keratinocytes was determined by the number of cells detected in a tested treated well as compared to the number of cells detected in a well in which the cells grew in Kmed medium without any DC or AE.

The number of cells in each well was determined by the microculture methylene blue assay as follows:

Extract treated cultures and controls were fixed in glutaraldehyde, 0.05% final concentration, for 10 mins. at room temperature. After washings the microplates were stained with methylene blue 1% in 0.1 M borate buffer pH 8.5 for 60 mins. at room temperature. Thereafter the plates were extensively and rigorously washed to remove excess dye and dried. The dye taken up by cells is eluted in 0.1 N HCl for 60 mins. at 37° C., and read at 620 nm.

In preliminary titration experiments linear readings were obtained for $1 \times 10^3$ to $4 \times 10^4$ cells/well. Each point of the growth curve experiments is an average of the reading of 5 wells, since keratinocytes grow in islands and do not form uniform monolayers. The number of average cells in the wells was determined at 2 days, and 5 days after incubation of the keratinocytes with the tested DC or AE as well as at 8 days after incubation (following 3 days growth without the tested extract).

(ii) Results:

As can be seen in FIG. 1A, DC IBR-1 from Narcissus bulbs had a significant inhibitory effect on the proliferation of keratinocytes. The inhibition was apparent from day 5 of the experiment and was dose dependent. Inhibition of the keratinocyte proliferation was apparent at a concentration as low as 0.5 µg/ml but was most significant at a concentration of 10 µg/ml of the DC. The effect was dose dependent (starting at a concentration of 1 g/ml of the DC and most effective at a concentration of 10 µg/ml of the DC).

Figure 1B:
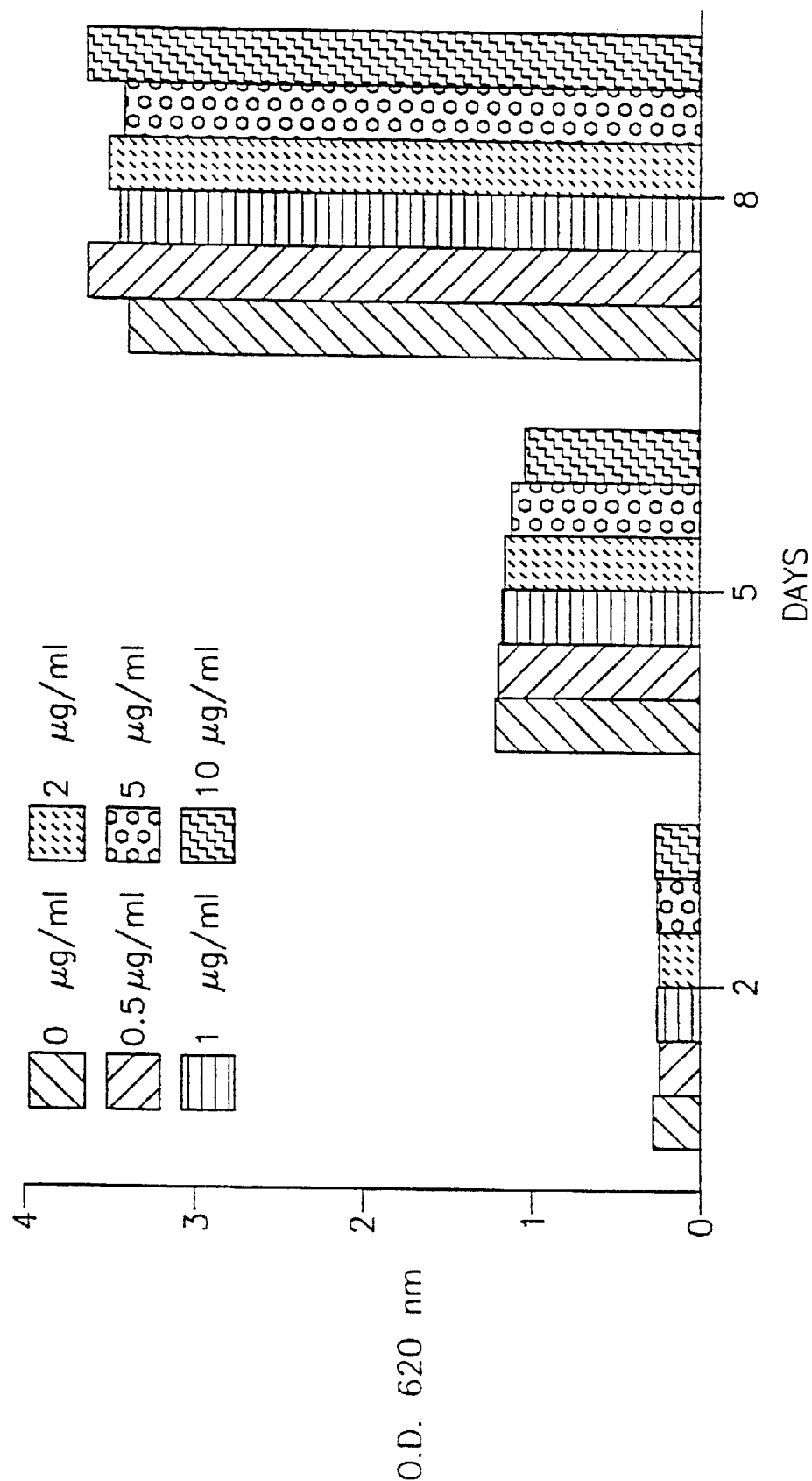

Against this, as seen in FIG. 1B, AE IBR-3 showed no significant inhibitory effect on the proliferation of keratinocytes.

Example III

Effect of DC Obtained From Dormant and Active Narcissus Bulbs on the Proliferation of Fibroblast in Culture (a) Preparation of Fibroblast Cell Cultures:

Primary fibroblast cell cultures were initiated from small human skin specimens and prepared as described in Example II above regarding preparation of keratinocyte cultures except that the growth medium used was DMEM+ 20% fetal calf serum.

(b) Preparation of DC and AE

DC IBR-1 and AE IBR-3 were prepared from dormant and active Narcissus bulbs as described above.

(c) Effect of DC and AE on Fibroblast Proliferation:

(i) Experimental assay:

The above extracts were added to the fibroblast cultures at various concentrations (1 g–10 g/ml) and the number of fibroblasts in the cultures was determined 2 days, 5 days and 8 days after the addition of the extracts to the cells as described in Example II(a) above.

Figure 2A:
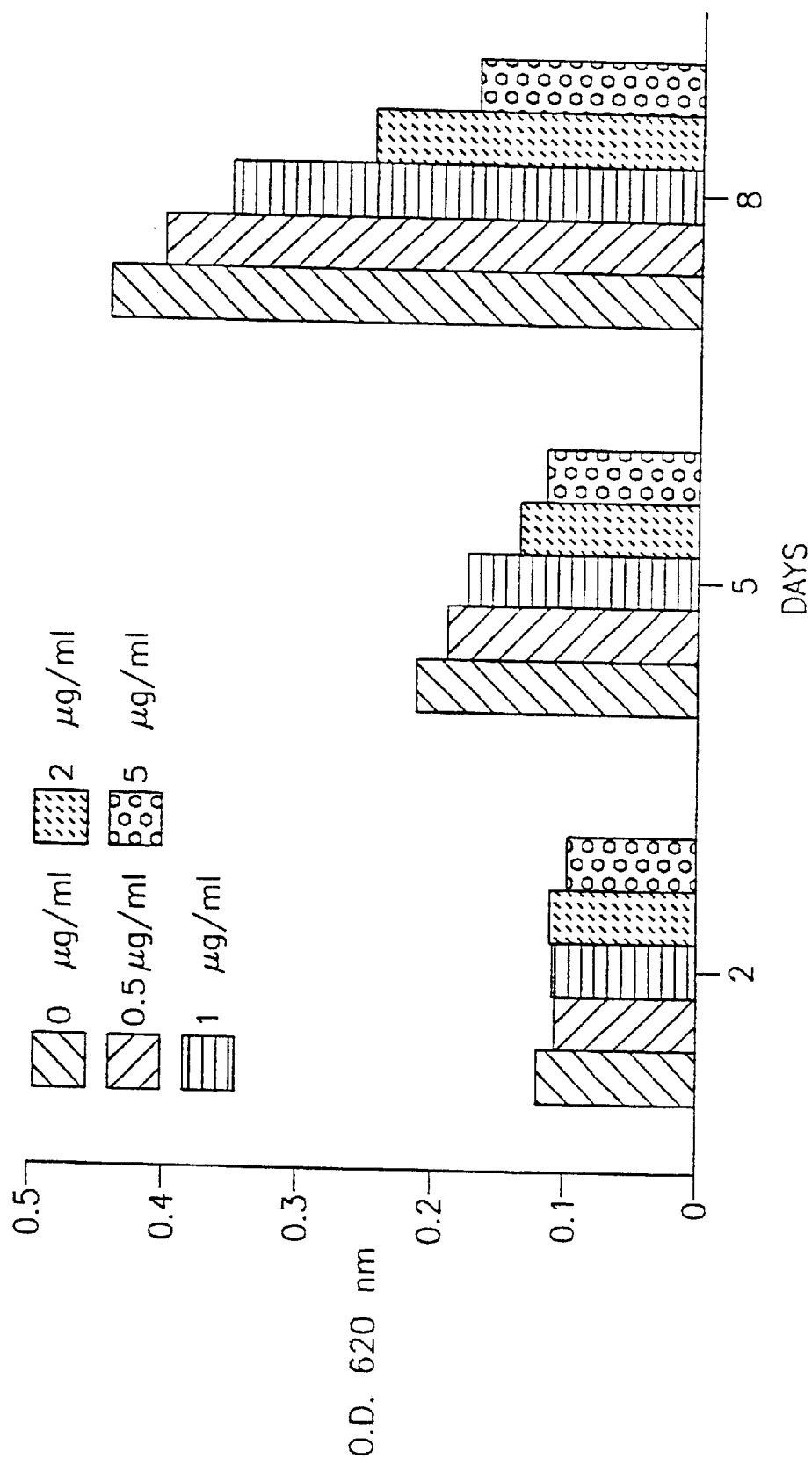
FIG. 2A—cells were incubated with the DC IBR-1 (dormant)

(ii) Results:

As seen in FIG. 2A, DC IBR-1 had the most significant inhibitory effect on the proliferation of fibroblast in culture. The effect was apparent from day 5 of the experiment and although was dose dependent, the effect was seen at doses as low as 0.5 µg/ml.

Figure 2B:
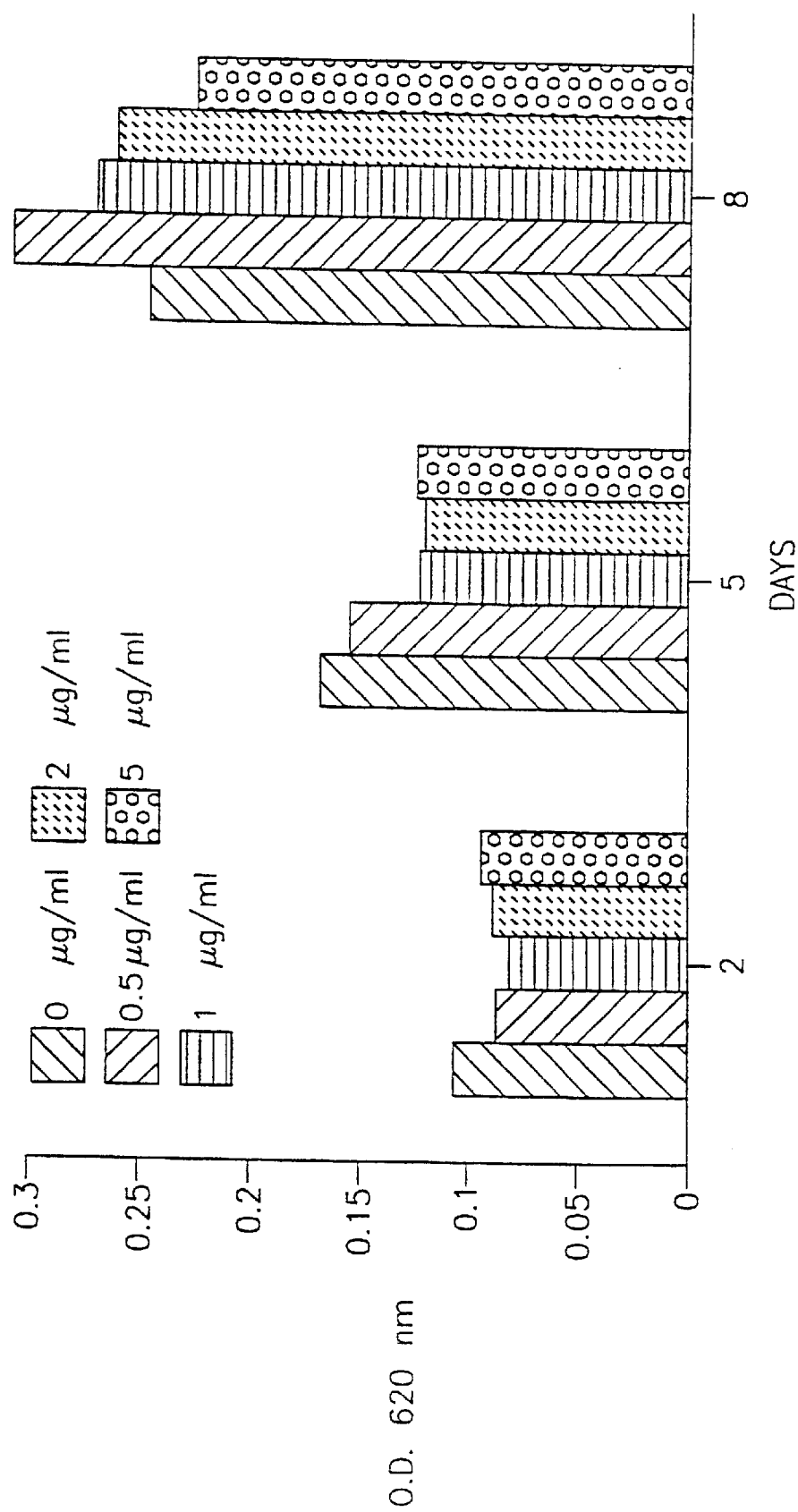
FIG. 2B—cells were incubated with the AE IBR-3 (active).

As can be seen in FIG. 2B, AE IBR-3 had no inhibitory effect on the proliferation of fibroblasts.

Example IV

Preparation of Cosmetic and Dermatological Compositions Comprising DC

The following are several specific examples of cosmetic and dermatological compositions which may be used in accordance with the invention for administration to an individual.

| | | |
|---|---|---|
| A. | Balm (topical route): | |
| | Ozokerite | 10 gr. |
| | Isopropyl palmitate | 9 gr. |
| | White vaseline | 14 gr. |
| | Preserving agent | 0.2 gr. |
| | Antioxidants | 0.3 gr. |
| | Perfume | 1 gr. |
| | DC prepared from bulb extract | 0.00001 gr. |
| | Liquid paraffin qs | 100 gr. |
| B. | Balm (topical route): | |
| | Ozokerite | 19 gr. |
| | Liquid purcellin oil | 10 gr. |
| | White vaseline | 15 gr. |
| | Preserving agent | 0.2 gr. |
| | Antioxidant | 0.3 gr. |
| | DC prepared from bulb extract | 0.00002 gr. |
| | Liquid paraffin qs | 100 gr. |
| C. | Emulsfied gel of O/W type (topical route): | |
| | Carbopol ® 981 (marketed by Goodrich) | 0.6 gr. |
| | Volatile silicone oil | 3 gr. |
| | Purcellin oil | 7 gr. |
| | Preserving agent | 0.3 gr. |
| | Ethyl alcohol | 15 gr. |
| | Perfume | 0.4 gr. |
| | Triethanolamine | 0.2 gr. |
| | DC prepared from bulb extract | 0.04 gr. |
| | Demineralized water qs | 100 gr. |
| D. | Aqueous-alcoholic gel (topical route): | |
| | Carbopol ® 981 (marketed by Goodrich) | 1 gr. |
| | Triethanolamine | 1 gr. |
| | 95% Ethanol | 60 gr. |
| | Glycerol | 3 gr. |
| | Propylene glycol | 2 gr. |
| | DC prepared from bulb extract | 5 gr. |
| | Demineralized water qs | 100 gr. |
| E. | Anhydrous gel (topical route): | |
| | Absolute ethanol | 61,1992 gr. |
| | Hydroxyethyl cellulose | 0.8 gr. |
| | Propylene glycol | 25 gr. |
| | Polyethylene glycol | 12 gr. |
| | DC prepared from bulb extract | 0.0008 g |
| F. | Emulsion of O/W type (topical route): | |
| | Volatile silicone oil | 10 gr. |
| | Liquid paraffin | 6 gr. |
| | Liquid lanolin | 3 gr. |
| | Arlacel ® 165 (marketed by Atlas) | 6 gr. |
| | Tween ® 60 (marketed by Atlas) | 2 gr. |
| | Cetyl alcohol | 1.2 gr. |
| | Stearic acid | 2.5 gr. |
| | Triethanolamine | 0.1 gr. |
| | Preserving agent | 0.3 gr. |
| | Antioxidants | 0.3 gr. |
| | DC prepared from bulb extract | 0.5 gr. |
| | Demineralized water qs | 100 gr. |
| G. | Emulsion of O/W type (topical route): | |
| | Propylene glycol | 2 gr. |
| | PEG 400 | 3 gr. |
| | Preserving agent | 0.3 gr. |
| | Carbopol ® 981 (marketed by Goodrich) | 0.2 gr. |
| | Isopropyl myristate | 1 gr. |
| | Cetyl alcohol | 3 gr. |
| | Stearic acid | 3 gr. |
| | Glycerol | 3 gr. |
| | Corn oil | 2 gr. |
| | Perfume | 0.5 gr. |
| | DC prepared from bulb extract | 0.001 gr. |
| | Demineralized water qs | 100 gr. |
| H. | Clear gel (topical route) | |
| | Oxyethylenated nonylphenol | 5 gr. |
| | Carbopol ® 981 (marketed by Goodrich) | 1 gr. |
| | Ethyl alcohol | 30 gr. |
| | Triethanolamine | 0.3 gr. |
| | Glycerine | 3 gr. |
| | Perfume | 0.3 gr. |
| | Preserving agent | 0.3 gr. |
| | DC prepared from bulb extract | 1 gr. |
| | Demineralized water qs | 100 gr. |
| I. | Cream containing liposomes (topical route): | |
| | Cetyl alcohol | 4 gr. |

-continued

|   |   |   |
|---|---|---|
|   | B-sitosterol | 4 gr. |
|   | Dicetyl phosphate | 0.5 gr. |
|   | Preserving agent | 0.3 gr. |
|   | Sunflower oil | 35 gr. |
|   | Perfume | 0.6 gr. |
|   | Carbopol ® 981 (marketed by Goodrich) | 0.2 gr. |
|   | Triethanolamine | 0.2 gr. |
|   | Sphingosine | 0.05 gr. |
|   | DC prepared from bulb extract | 0.2 gr. |
|   | Demineralized water qs | 100 gr. |
| J. | Per os composition: |   |
|   | Talc | 5 mg |
|   | Aerosil 200 | 5 mg |
|   | Stearate de Zn | 5 mg |
|   | DC prepared from bulb extract | 3 mg |
|   | Lactose qs | 400 mg |
| K. | Liquid of Iontophoresis: |   |
|   | Benzoate de sodium | 2 mg |
|   | Preserving agent | 0.15 gr. |
|   | DC prepared from bulb extract | 1 gr. |
|   | Water qs | 100 gr. |
| L. | Emulsion W/O: |   |
|   | Protegin (marketed by Goldschmidt) | 19 gr. |
|   | Vaseline oil | 8 gr. |
|   | Glycerine | 3 gr. |
|   | DC prepared from bulb extract | 1 gr. |
|   | Sulfate de Mg | 0.5 gr. |
|   | Perfume | 0.8 gr. |
|   | Preserving agent | 0.2 gr. |
|   | Water qs | 100 gr. |

Example V
Extracts Prepared From Narcissus Bulblets (Cell Cultures) on Cucumber seedling growth:

(a) Preparation of Narcissus Bulb Cell Cultures

Active Narcissus bulbs from the field having inflorescence stalk initials were used to prepare duplicate inner scale explants. The explants were then inoculated into NR31 medium (NAA/10 μM BA: 5:0.5 μM) to initiate callus cultures. Four to 5 weeks after the initiation of the callus cultures, the cultures were transplanted into NR8 medium (6% sucrose) to form bulblets growth explants. For scaling up of the biomass, half bulblets were transplanted into bulblet column bioreactors with liquid basal media N4 comprising:

| Murashige & Skoog (Sigma M-5525) | 4.33 gr/L |
|---|---|
| Myoinositol | 100 mg/L |
| Adenine sulfate | 150 mg/L |
| $NaH_2PO_4H_2O$ | 345 mg/L |
| NAA | 5 μM Agar Type A 7 gr/L |
| BA | 5 μm pH = 5.7 |
| Pyridoxine | 1 mg/L |
| Glycine | 2 mg/L |
| Nicotinic acid | 5 mg/L |
| Thiamine HCl | 0.5 mg/L |
| Sucrose | 30 gr/L | for a period of 4 weeks.

(b) Preparation of Cell Culture Derived DC

The plant material prepared as described in (a) above was then shaken for 7–10 days on a gyratory shaker at about 35° C. (the column weight per medium was 0.1 gr/ml). Half of the cell cultures were induced into dormancy by their incubation at a high temperature (of about 35° C.). The DC prepared from such cultures was designated IBR-11. The remaining cell cultures were maintained in their active state by growing them in regular conditions and the AE prepared from them was designated IBR-10. AE IBR-10 or DC IBR-11 were prepared from the medium free bioimass which was washed with water, weighed and homogenized in an ultra-Turbo-turax. The homogenate was suspended and diluted in steril distilled water.

(c) Cucumber seeds cv. "Delila", 1994–1995, 95% germination, 99.9% purity were germinated in tap water at 27° C. in the dark for about 20 hours until root initiation (1–2 mm).

(d) The Experimental Assay:

(i) The effect of the above DC and AE prepared from Narcissus bulblets on root elongation and hypocotyl elongation of the cucumber seedlings was determined as follows. Each experimental group consisted of petri dishes each containing 10 seeds was incubated with:

1. DC IBR-11 (dormant)
2. AE IBR-10(active).

One or two layers of filter paper were placed in each of the petri dishes and 10 cucumber seeds, germinated as explained above, were placed on the filters. The Petri dishes were incubated for 72 hours at 27° C. to 30° C. in the dark.

The effect of extracts was tested on two parameters of the cucumber seeds:

1. Root elongation
2. Hypocotyl elongation.

These two parameters were tested after 72 hours of incubation of the seeds with the extract.

(ii) Results:

As seen in Table 5 below, 72 hours after incubation, DC IBR-11 had a significantly higher inhibition activity on both the root length and hypocotyl length of the seedlings as compared to the effect of AE on the seedlings' growth.

TABLE 5

|   | AE (IBR-10) | DC (IBR-11) | % inhibition of DC compared to AE $\frac{(AE) - (DC)}{(AE)} \times 100$ |
|---|---|---|---|
| Root length (mm) 72 h | 86 | 31 | 58% |
| Hypocotyl (mm) 72 h | 81 | 49 | 40% |

Example VI
Effect of Narcissus Bulb Cell Culture Derived DC on Proliferation of Keratinocytes (a) Preparation of Keratinocyte Cultures Human keratinocyte cultures were prepared as described in Example II(a) above.

(b) Effect of Narcissus Bulblet Derived DC on the Proliferation of Keratinocytes (i) Experimental assay:

Narcissus bulb derived cell cultures were obtained as described above and DC IBR-11 was prepared from bulblets induced into dormancy (as is also described above).

The secondary keratinocyte cell cultures seeded in microplates as described above, were further grown in Kmed for a period of 3–4 days. The microplates were then divided into the following main groups:

(1) keratinocytes which were continuously grown in Kmed; and
(2) keratinocytes grown in Kmed containing DC IBR-11 in several concentrations (from 0.5 μg/ml-10 μg/ml, each concentration forming a separate experimental group).

Each experimental group contained 5 wells. The growth medium containing DC was changed every 24 hours for a period of 5 days after which the medium was removed from all of the wells and fresh Kmed medium without any plant extract was added and the cultures were grown in it for an additional 3 days.

The effect of the tested DC on the proliferation of the keratinocytes was determined by the number of cells detected in a tested treated well as compared to the number of cells detected in a well in which the cells grew in Kmed medium without any DC.

The number of cells in each well was determined by the microculture methylene blue assay as follows:

Extract treated cultures and controls were fixed in glutaraldehyde, 0.05% final concentration, for 10 mins. at room temperature. After washing, the microplates were stained with methylene blue 1% in 0.1 M borate buffer pH 8.5 for 60 mins. at room temperature. Thereafter the plates were extensively and rigorously washed to remove excess dye and dried. The dye taken up by cells is eluted in 0.1 N HCl for 60 mins. at 37° C., and read at 620 nm.

In preliminary titration experiments linear readings were obtained for $1 \times 10^3$ to $4 \times 10^4$ cells/well. Each point of the growth curve experiments is an average of the reading of 5 wells, since keratinocytes grow in islands and do not form uniform monolayers. The number of average cells in the wells was determined at 2 days, and 5 days after incubation of the keratinocytes with the tested DC as well as at 8 days after incubation (following 3 days growth without the tested extract).

Figure 3:
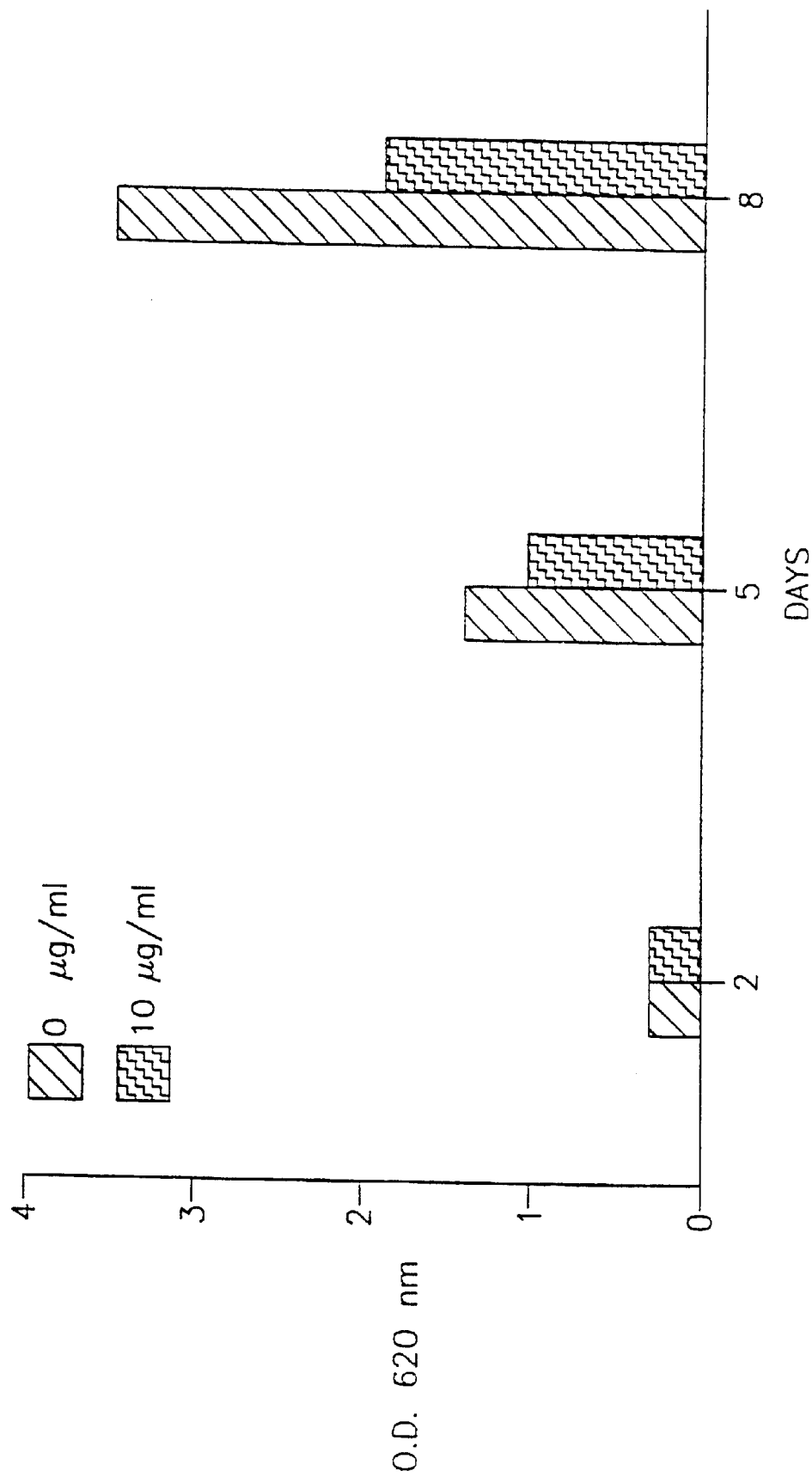
FIG. 3 is a histogram showing the number of keratinocytes in a microculture at different periods of time after their incubation with various concentrations of the cell culture derived DC IBR-11. As control, the cells were incubated with growth medium only (0 µg/ml DE IBR-11). The number of cells in each well was determined by the microculture methylene blue assay (described in Example II) and the dyed culture plates were read as 620 nm.

(ii) Results:

As can be seen in FIG. 3, DC IBR-11 showed significant inhibitory activity on the proliferation of keratinocytes in culture.

Example VII

Effect of DC obtained from dormant Narcissus bulblets on the proliferation of fibroblast in culture (a) Preparation of Fibroblast Cell Cultures:

Primary fibroblast cell cultures were initiated from small human skin specimens and prepared as described in Example II above regarding preparation of keratinocyte cultures except that the growth medium used was DMEM+ 20% fetal calf serum.

(b) Preparation of Cell Cultured DC:

IBR-11 was prepared from dormant bulblets as described in Example V(b) above.

(c) Effect of DC on Fibroblast Proliferation:

(i) Experimental assay:

The above extracts were added to the fibroblast cultures at various concentrations (1 µg–10 µg/ml) and the number of fibroblasts in the cultures was determined 2 days, 5 days and 8 days after the addition of the extracts to the cells as described in Example V(a) above.

Figure 4:
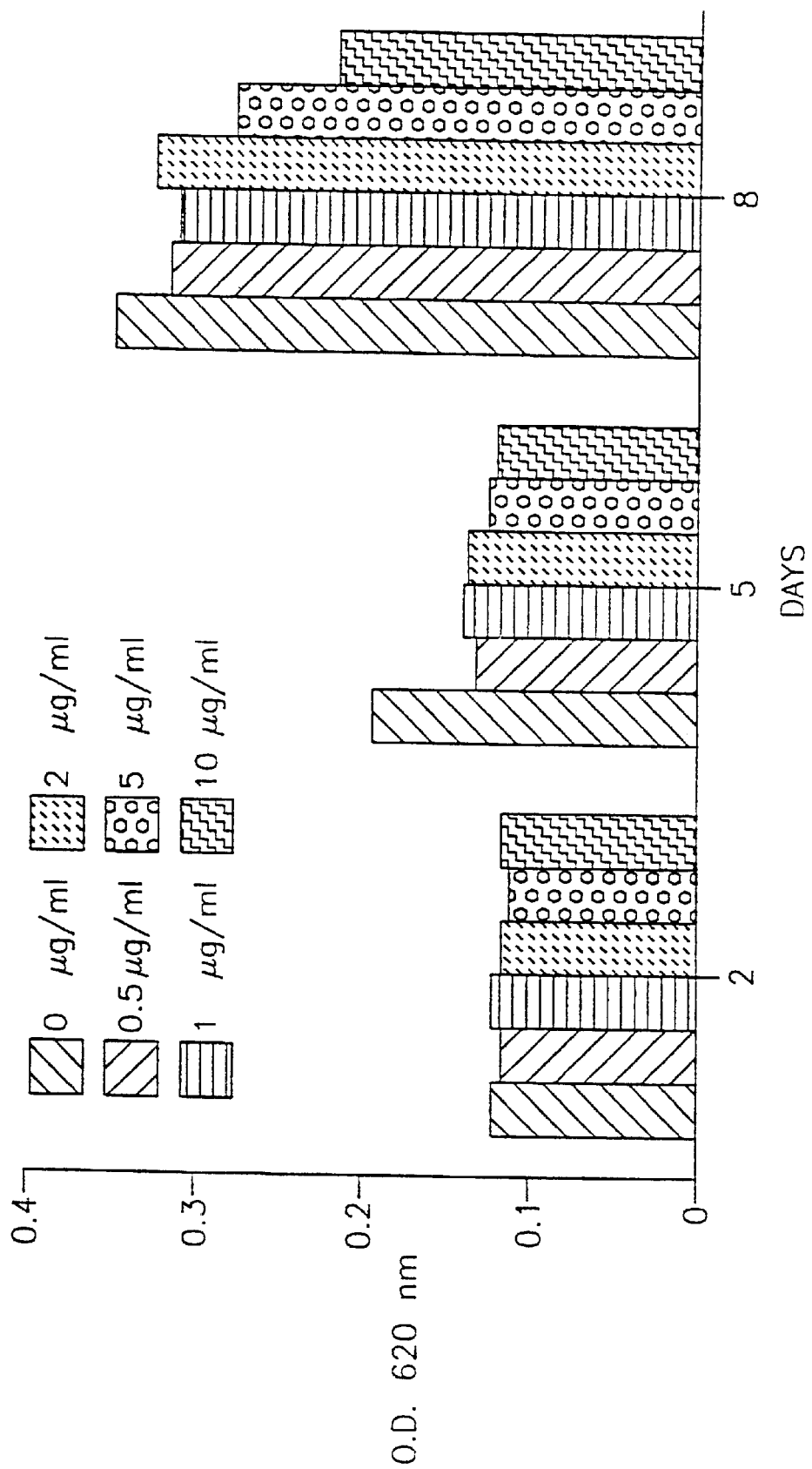
FIG. 4 is a histogram showing the number of fibroblasts in a microculture at different periods of time after their incubation with various concentrations of the cell culture derived DC IBR-11.

(ii) Results:

As can be seen in FIG. 4, the cell culture derived DC IBR-11 showed inhibitory activity on the proliferation of fibroblasts.

Example VIII

Effect of Fruit Juice on Cucumber Seed Growth (a) Preparation of Fruit Juice

Grapefruit juice was produced from one fresh grapefruit and the produced juice was squeezed and filtrated through cotton cloth and then centrifuged at 10,000 rpm for 10 mins. at room temperature. The supernatant was then used for testing its effect on cucumber seed growth as described below.

(b) The Effect of Grapefruit Juice on Growth of Cucumber Seedlings:

(i) Experimental assay:

Cucumber seeds were prepared as described in Example 1 (c)(i) above. Each experimental group comprised ten Petri dishes which were filled with 1.8 ml of the following:

(1) $dH_2O$ (2) Fruit juice obtained as in (a) above.

One or two layers of filter paper were placed in each of the petri dishes and 10 cucumber seeds, germinated as explained above, were placed on the filters. The petri dishes were incubated at 25° C. and the parameters of the cucumber seeds were measured at 24 hours and 72 hours after beginning of incubation.

The effect of the fruit juice was tested on two parameters of the cucumber seeds:

(1) Root elongation (2) Hypocotyl elongation (ii) Results:

As seen in Table 6 below, this experiment indicates that the fruit juice comprises inhibitory activity on the growth of cucumber seeds.

TABLE 6

| Treatment | 72 hours | | 72 hours % inhibition | |
| --- | --- | --- | --- | --- |
| | Root mm | Hypocotyl mm | Root mm | Hypocotyl mm |
| $dH_2O$ | 110 | 35 | — | — |
| Grapefruit Juice | 3 | 0 | 97 | 100 |

Example IX

Effect of Dorman Extract Obtained From the Crustacean *Artemia salina* on Cucumber Seed Growth (a) Preparation of Extracts From *Artemia salina*:

The dorman extract designated IBR-4 was obtained by preparing an extract from *Artemia salina*. The Artemia "eggs" may be submitted to dehydration or high salt concentration resulting in opening of their shell which is then followed by their grounding. Alternatively, the Artmeia eggs may be dispensed in 10 ml of water resulting in softening of the shell. Following grounding or softening of the shells, the eggs are then dissolved in one of any of solvents known per se (e.g. water) to obtain an extrct from them. The extract may be lyophilized (as in this example) or alternatively, used as obtained. An additional method of obtaining the Artemia extract may be to dissolve the Artemia eggs in water until the prenauplius larvae crawl out of the shells after which the larvae are grounded and an extract obtained therefrom.

(b) The Effect of the DC Extract From Artemia (IBR-4) on Growth of Cucumber seedlings:

(i) Experimental assay:

Cucumber seeds were prepared and seeded into petri dishes as explained in Example 1 above. Each experimental group comprised a petri dish containing 10 cucumber seeds and the results shown below are an average of the parameters measured for the 10 seeds. The petri dishes were grown at 28° C. in the dark and the root length and hypocotyl length of the cucumber seeds were measured 24 hours and 48 hours after beginning of incubation with 1.8 ml of one of the following:

(1) $dH_2O$ (2) DC IBR4 at a concentration of 0.02 gr./ml.

(ii) Results:

As seen in Table 7 below, the Artemia dorman extract IBR-4 had a significant inhibitory effect on cucumber seed growth which was apparent already after 24 hours of incubation of the seeds with the DC IBR4 but was most significant 48 hours after incubation (66% inhibition on root growth and 40% inhibition on hypocotyl growth).

TABLE 7

| Treatment | 24 hours | | 24 hours % Inhibition | | 48 hours | | 48 hours % inhibition | |
|---|---|---|---|---|---|---|---|---|
| | Root mm | Hypocotyl mm | Root | Hypocotyl | Root mm | Hypocotyl mm | Root | Hypocotyl |
| dH$_2$O | 35 | 4 | 0 | 0 | 61 | 10 | 0 | 0 |
| IBR4 0.02 gr/ml | 20 | 3 | 43 | 25 | 21 | 6 | 66 | 40 |

Example X
Effect of a Dorman Extract From a Dormant Plant (Narcissus Derived IBR-1) and a Dorman Extract Obtained From Animals (Artemia Derived IBR-4) on Proliferation of Mouse Bladder Carcinoma Cells (a) Preparation of the Dorman Extracts:

The Narcissus derived plant dorman extract IBR-1 and the Artemia derived animal dorman extract IBR-4 were prepared as explained in the Examples above.

(b) The Effect of DC IBR-1 and DC IBR-4 on Proliferation of Mouse Bladder carcinoma cells:

(i) Experimental assay:

The two experiments were carried out as follows:

T24P cells (mouse bladder carcinoma cells) (FIG. 5) were plated at a concentration of 5×10$^4$ cells/well in a microculture well and T50 cells (mouse bladder carcinoma cells) (FIG. 6) were plated at a concentration of 2×10$^4$ cells per well in a microculture plate and the cells were grown in cell culture medium.

DC IBR-1 and DC IBR-4 were added to the T24P cell cultures and IBR-1 was added also to the T50 cells at various concentrations (0 g/ml–25 g/ml) 24 hours after plating of the cells and 48 hours after the beginning of incubation of the cells with the dorman extracts. The number of cells per well were determined 48 hours after the beginning of incubation of the cells with the extracts using the microculture methylene blue assay (described in Example 2 above) and the dyed culture plates were read at 620 nm.

Figure 5A:
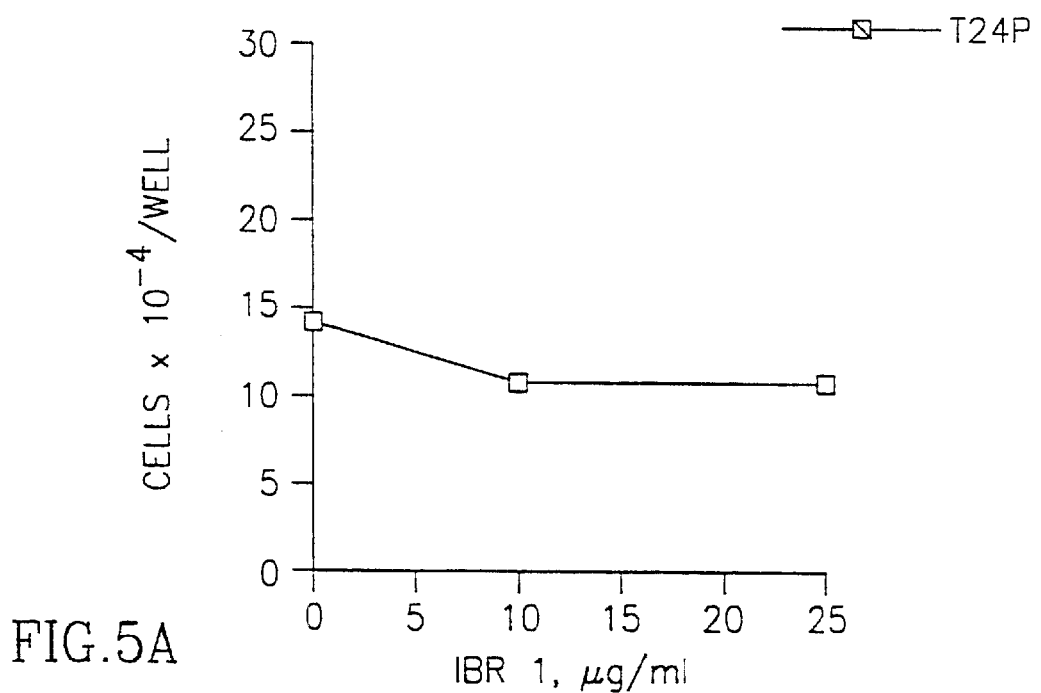
FIG. 5 is a graphic representation showing the number of cultured mouse bladder carcinoma cells (T24P) in a microculture 72 hours after their incubation with various concentrations of a plant derived DC (IBR-1) (FIG. 5A) or an animal derived DC (IBR-4) (FIG. 5B). The number of cells in each well was determined by the microculture methylene blue assay (described in Example 2) and the dyed culture plates were read at 620 nm.
Figure 5B:
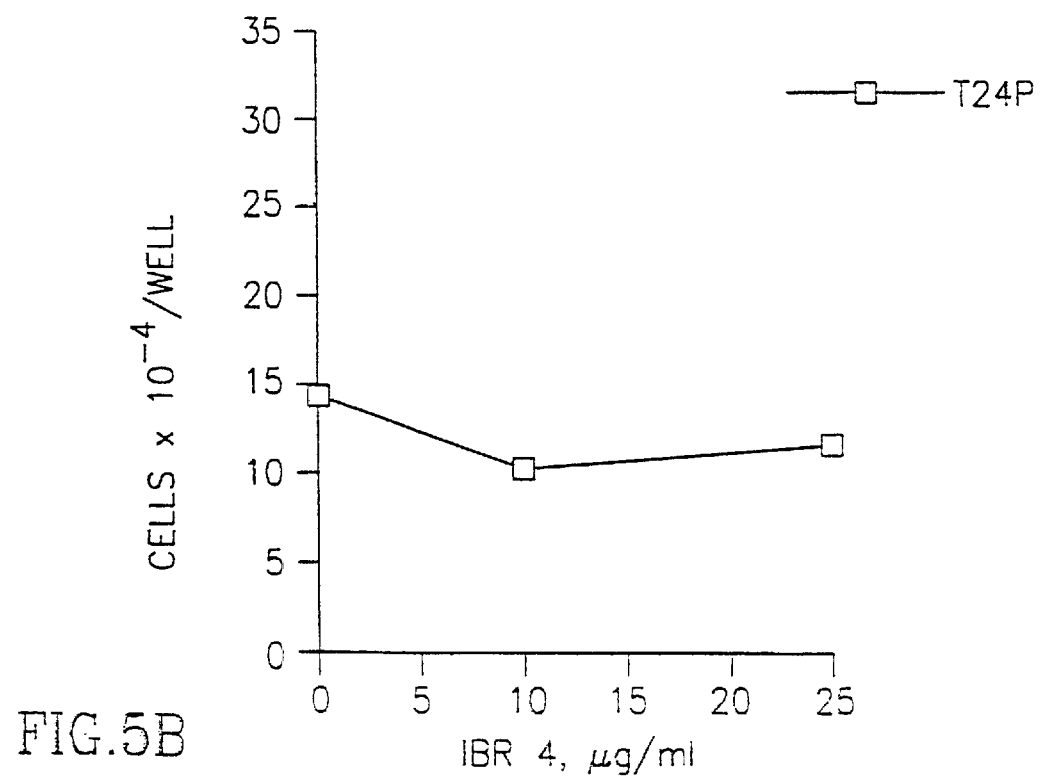
Figure 6:
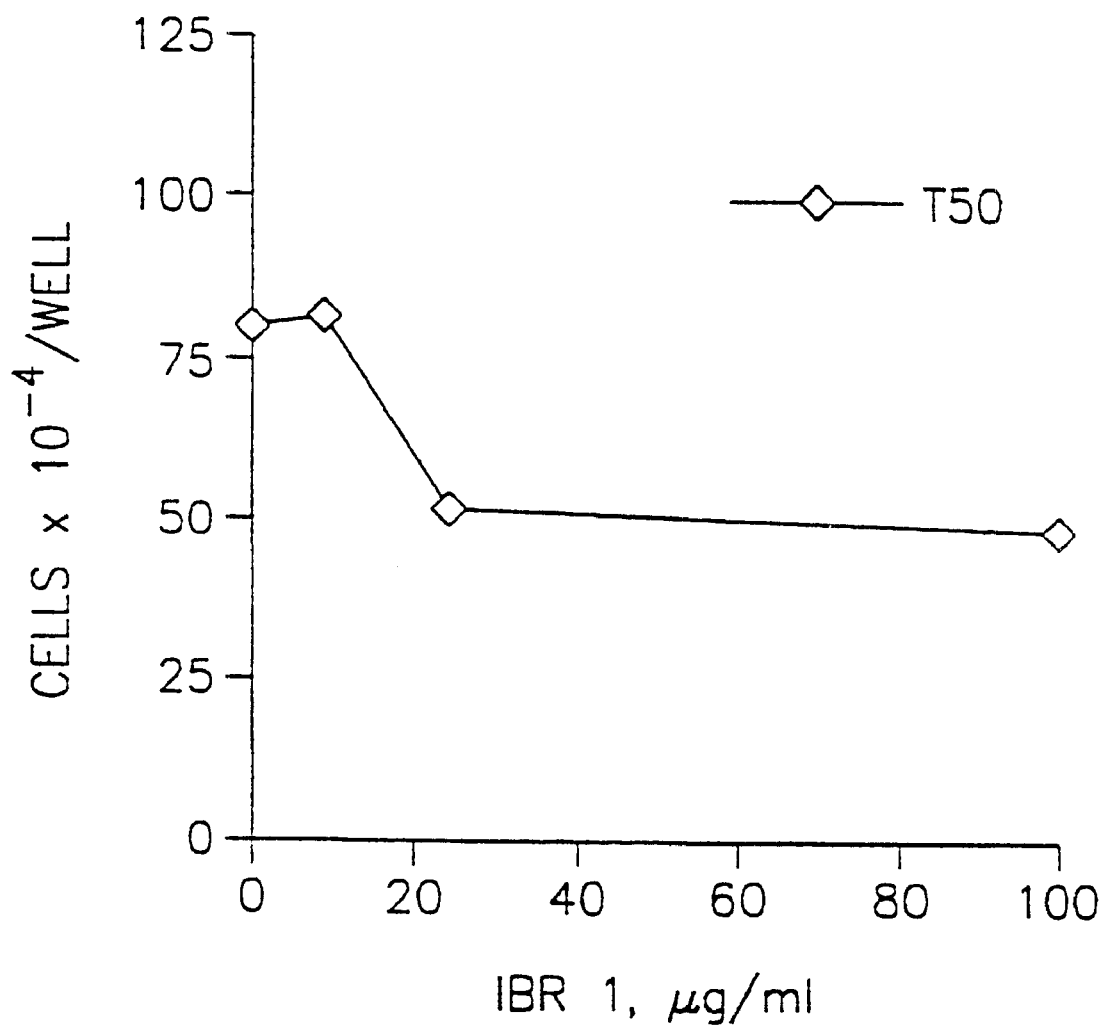
FIG. 6 is a graphic presentation showing the number of mouse bladder carcinoma cells (T50) in a microculture at different periods of time after their incubation with various concentrations of DC IBR-1. The dorman extracts were added at day 1 and day 3 of the cell culture and the number of cells in each well were determined on day 5 of the culture as described in FIG. 5 above. The number of cells in each tested well was determined by using the microculture methylene blue assay as explained in the description of FIG. 1 above and by reading of the dyed microculture plate at 620 nm.

(ii) Results:

As seen in FIGS. 5 and 6, both the plant derived dorman extract as well as the animal derived dorman extract had some inhibitory effect on the proliferation of mouse bladder carcinoma cells T24P (FIG. 5) and T50 (FIG. 6).

Example XI
Inhibition of Cucumber Seed Growth by Grape and Kiwi Juice (a) Preparation of Fruit Juice Grape and Kiwi juices were produced from fresh fruit by blending the fruit in the blender cup for 3 mins. at high speed, filtrating the blend through a cheese cloth and centrifuging it at 6,500 rpm for 10 mins. at room temperature. The supernatant was then used for the experiment at a concentration of 1.2 gr/ml of the grape juice and 1.26 gr/ml of the kiwi juice. The concentration was determined by fruit original weight (gr.) for final volume (v). Several dilutions of each juice were prepared and used for testing on cucumber seed growth.

Preparation of the cucumber seeds and the experimental assay were carried out as described in Example I(c)(i) above. The length of the roots and hypocotyls were measured 24 and 48 hours after beginning of incubation of the seeds with each of the tested juices or controls at 28° C. As seen in Table 8 below, both the kiwi juice and the grape juice showed a very high percent of inhibition both on growth of cucumber roots as well as on hypocotyls. The most prominent inhibition was seen 48 hours after beginning of incubation wherein both juices inhibited the growth of the cucumber seeds.

TABLE 8

| | 24 h | | 48 h | |
|---|---|---|---|---|
| | | | | Hypocotyl |
| | Root % Inhibition | Hypocotyl % Inhibition | Root % Inhibition | % Inhibition |
| dH$_2$O | 0 | 0 | 0 | 0 |
| Kiwi juice 100 mg/ml | 50 | 100 | 72 | 100 |
| Kiwi juice 50 mg/ml | 33 | 67 | 55 | 63 |
| Kiwi juice 25 mg/ml | 0 | 67 | 42 | 38 |
| Kiwi juice 5 mg/ml | 0 | 0 | 7 | 13 |
| Grape juice 100 mg/ml | 83 | 100 | 88 | 100 |
| Grape juice 50 mg/ml | 40 | 100 | 67 | 63 |
| Grape juice 25 mg/ml | 17 | 67 | 42 | 63 |
| Grape juice 5 mg/ml | 10 | 17 | 20 | 25 |

Example XII
Cell Cycle Analysis of Cells After Incubation with DC (i) Experimental Assay:

Cell cultures of keratinocytes obtained from healthy human adults and cell cultures of fibroblasts obtained from healthy human skin preparations were incubated with Narcissus derived DC (IBR-1), Narcissus derived AE (IBR-3) and Artemia derived DC (IBR-4) at various concentrations. The DNA content of the cells was analyzed by FACS using ethidium iodide as the fluorescent dye which binds to the DNA (Parks D. R., and Herzenberg, L. A., In: Methods in Cell Biology, Vol. 26, Academic Press, p. 283, 1982). The analysis was carried out on day 2 and 5 after beginning of incubation of the cells with the various extracts and was carried out with FACS FPAR-Plus (Becton-Dickinson, Inc.)

In addition, the percent apoptosis in each cell culture incubated with the various DC exacts was also determined. In general, apoptosis begins with a strong mitochondrial activation followed by a cellular nuclear degradation. FACS analysis of the above cell cultures enabled also to calculate the percent apoptosis in each cell culture.

Figure 7A:
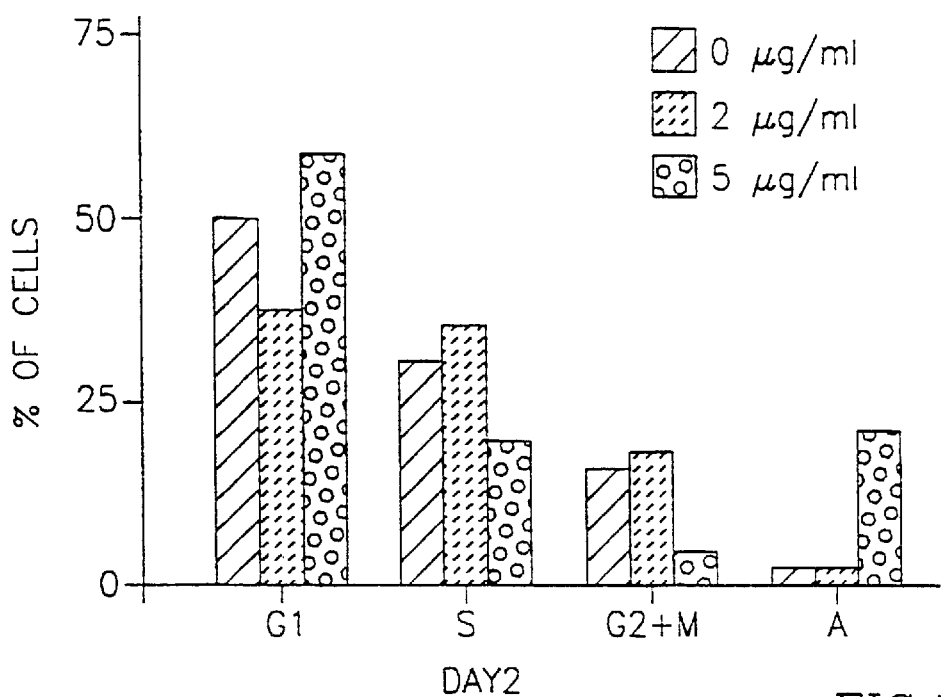
FIG. 7 is a histogram showing the DNA content analysis of keratinocytes incubated with DC IBR-1 for 2 and 5 days (7A and B, respectively) AE IBR-3 (7C and D, respectively) and DC IBR-4 (7E and F, respectively). The analysis was carried out with a FACS, FPAR-Plus (Becton-Dickinson, Inc.) using ethidium bromide. The percent of cells being in the G1 phase, S phase and $G_2$+M phase was determined in each cell culture. In addition, the percent of apoptosis (A) in each culture was also determined.
Figure 7B:
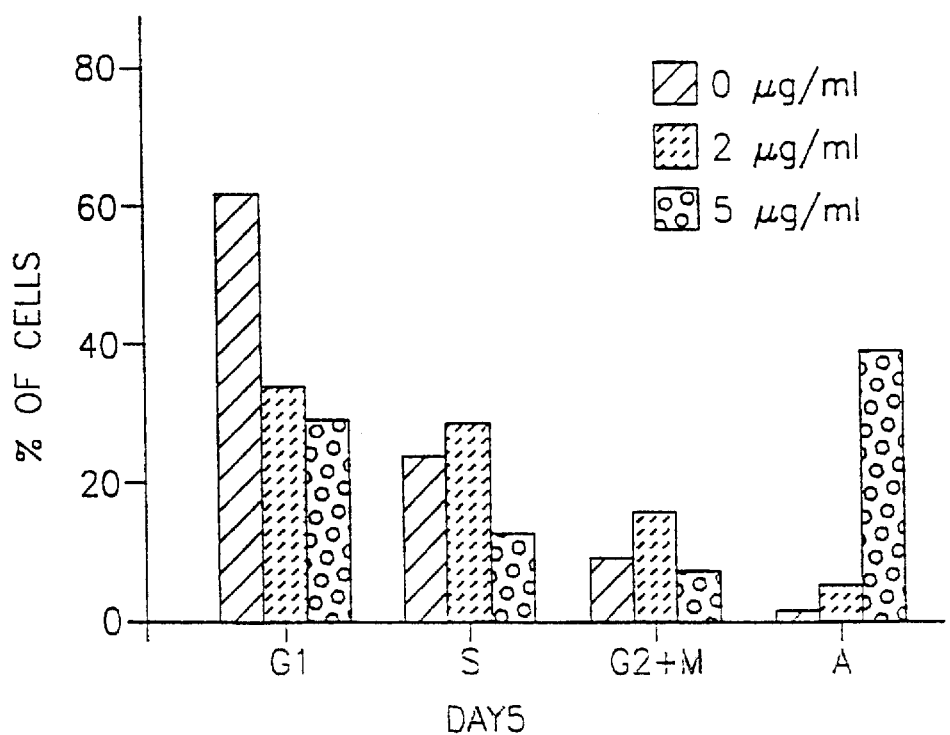
Figure 7C:
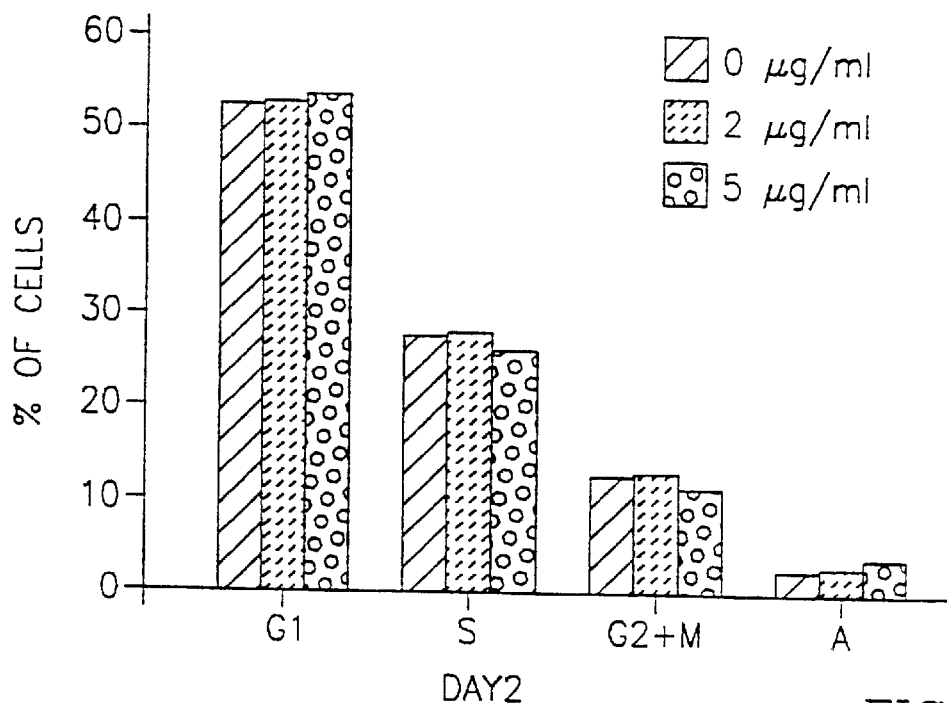
Figure 7D:
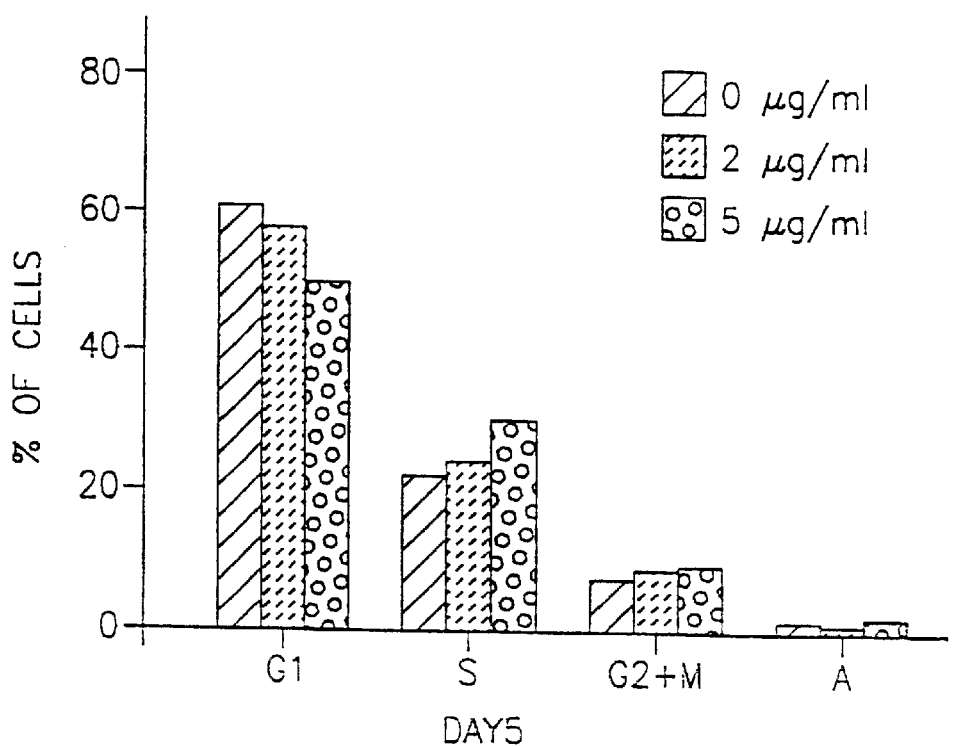
Figure 7E:
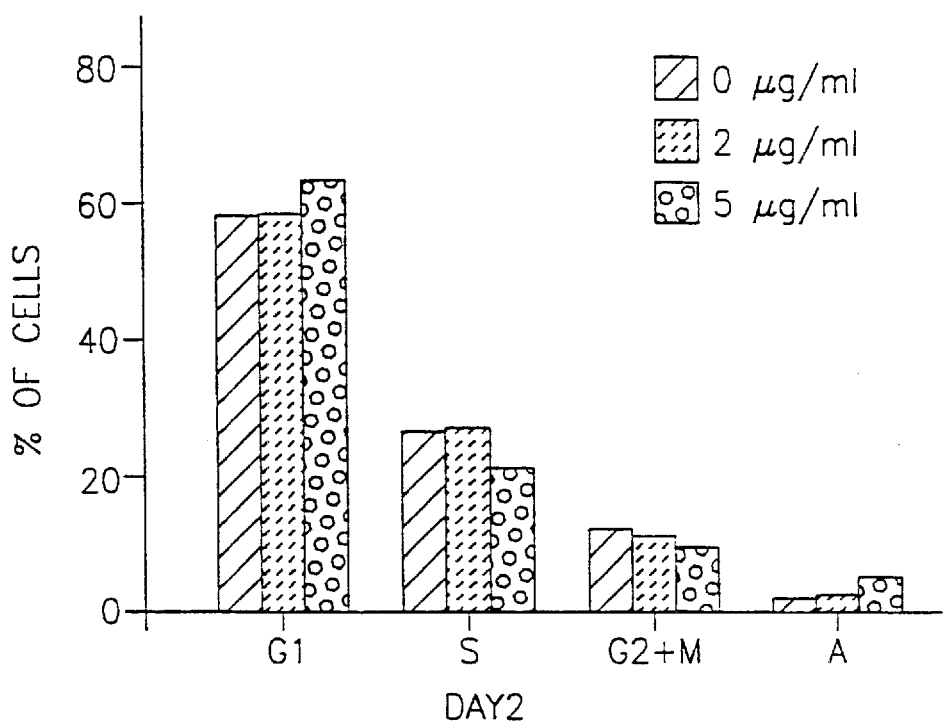
Figure 7F:
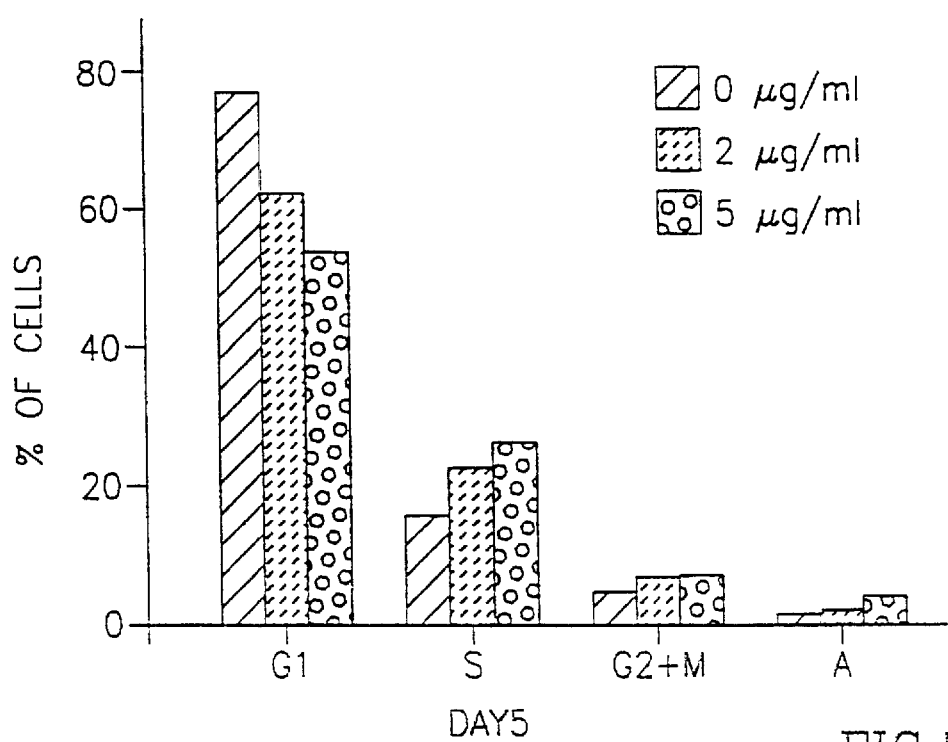

(ii) Results:

(a) Effect of DC on the cell cycle of keratinocytes:

As seen in FIGS. 7A and B, and in FIGS. 7E and F, both Narcissus derived DC and Artemia derived DC had an effect on the DNA content of the keratinocytes which showed a decrease in percent of cells being in the G1 phase and an increase in cells being in the S and G$_2$+M phases (the effect being evident already on day 2 of the incubation and more apparent on day 5 of the incubation). Against this, as seen in FIGS. 7C and D, the effect of the Narcussis derived AE (IBR-3) was much less apparent being slightly evident only 5 days after incubation where a decrease in the percent of cells in the G1 phase was seen with an increase in the percent of cells being in the S phase and a non significant increase in the percent of cells being in the $G_2+M$ phase.

In addition, the keratinocytes incubated with the Narcissus and Artemia derived DCs IBR-1 and IBR-4, showed an increase in the percent of apoptosis while no such increase was seen in keratinocytes incubated with Narcissus derived AE IBR-3.

(b) Effect of DC on the cell cycle of fibroblasts

Figure 8A:
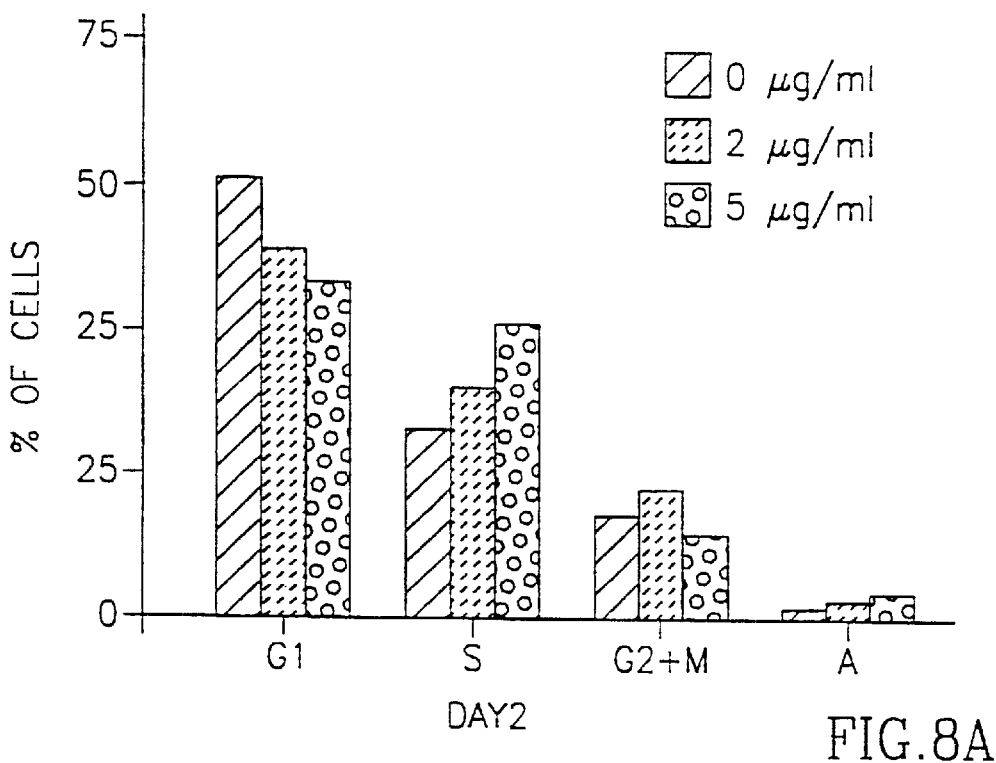
FIG. 8 is a histogram showing the DNA content analysis of fibroblast incubated with DC IBR-1 for 2 and 5 days (FIGS. 8A and B), AE IBR-3 (FIGS. 8C and D) and DC IBR-4 (FIGS. 8E and F). The analysis was carried out as described in FIG. 7 above.
Figure 8B:
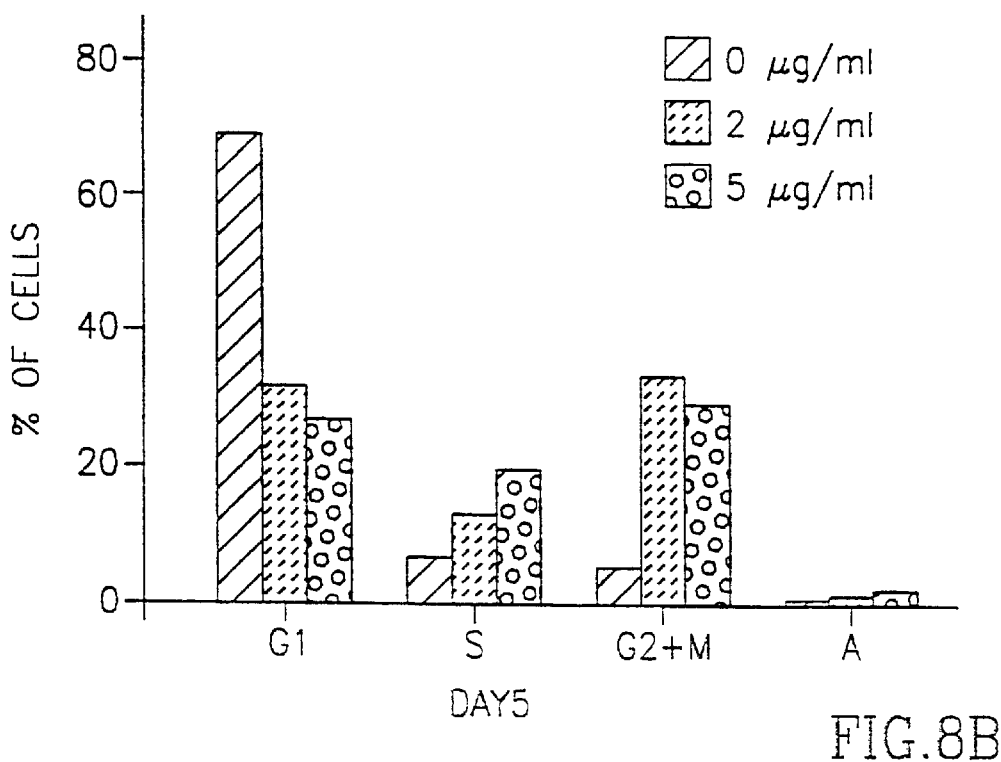
Figure 8C:
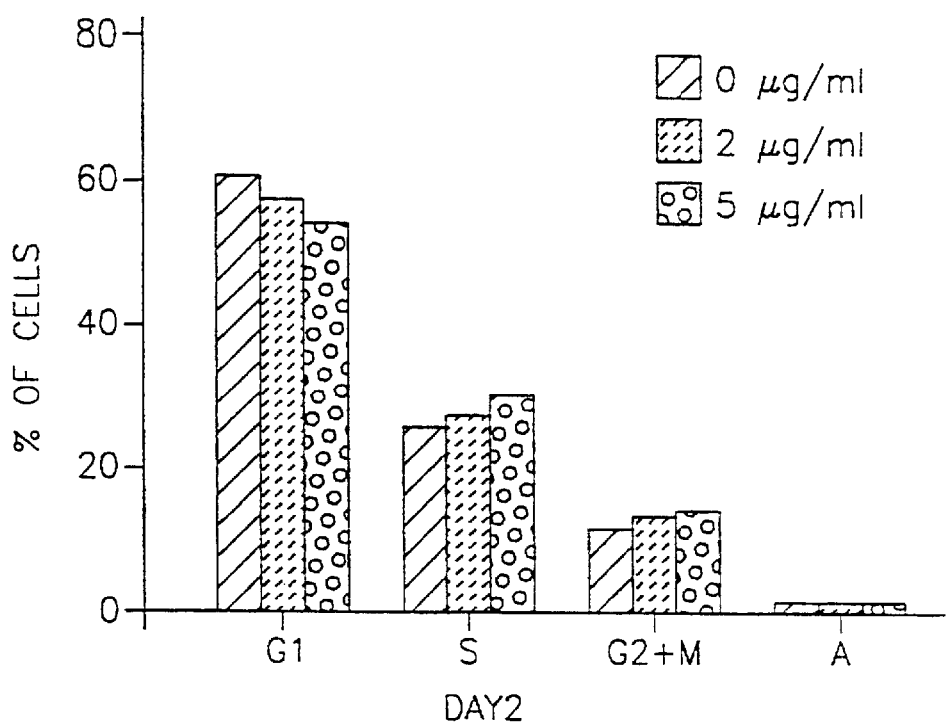
Figure 8D:
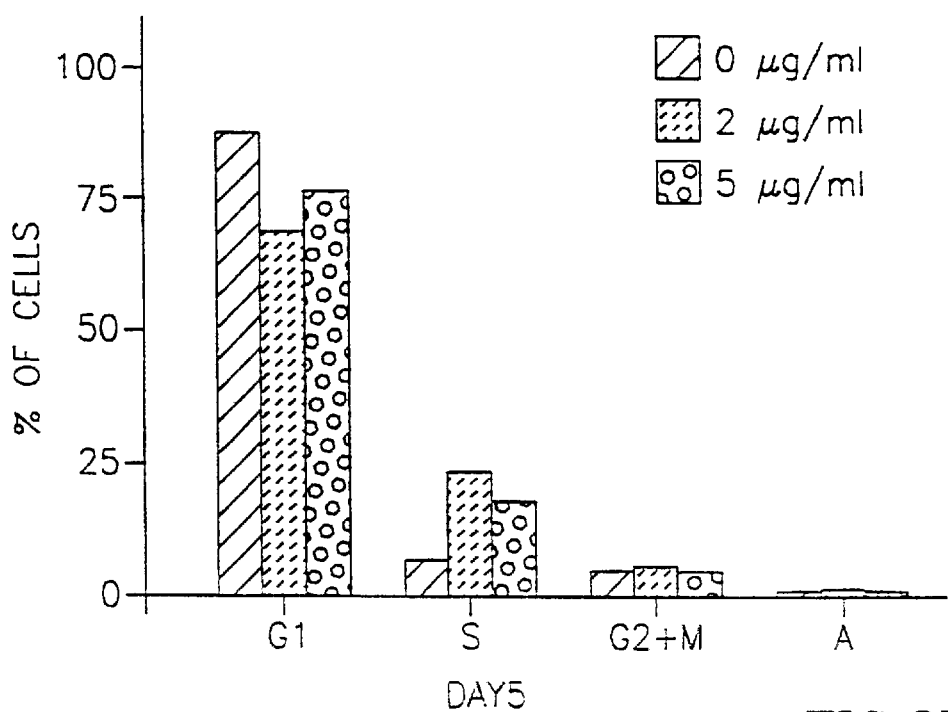
Figure 8E:
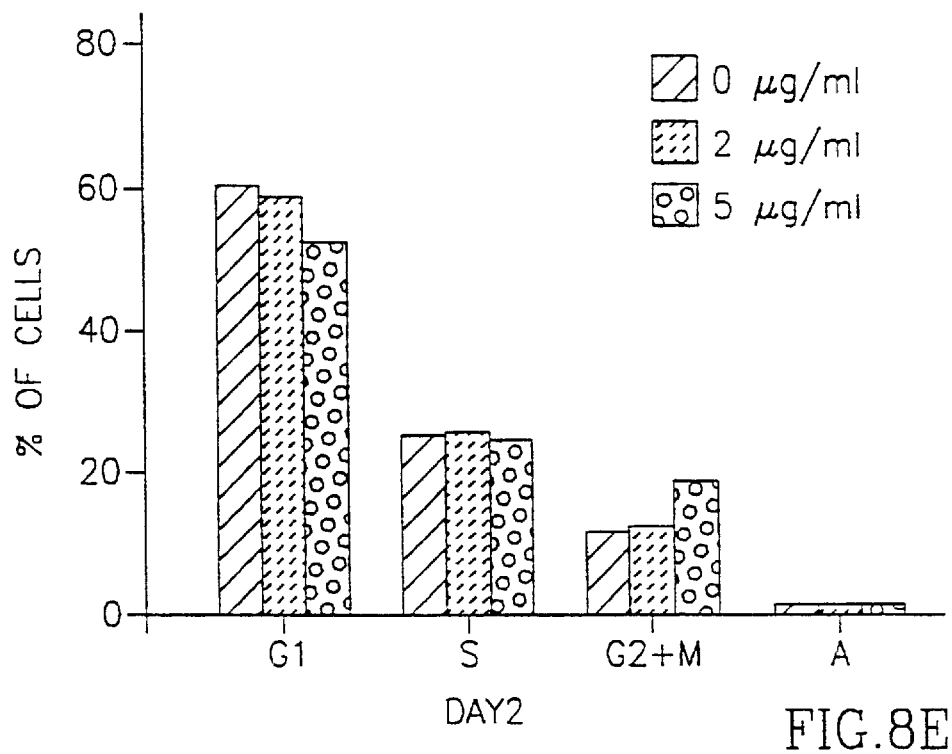
Figure 8F:
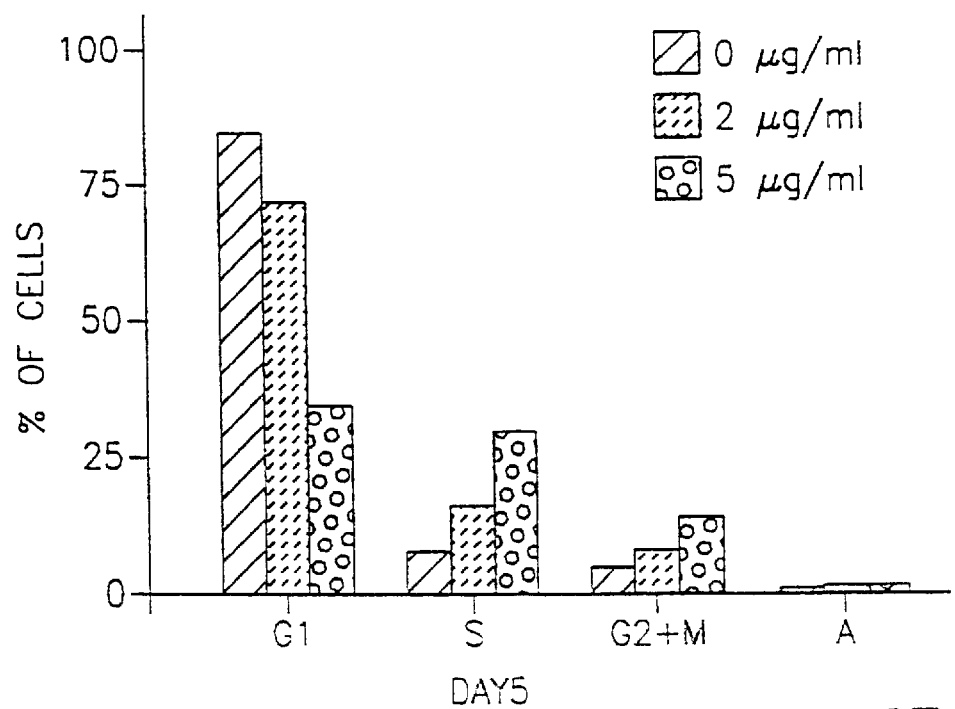
Figure 9A:
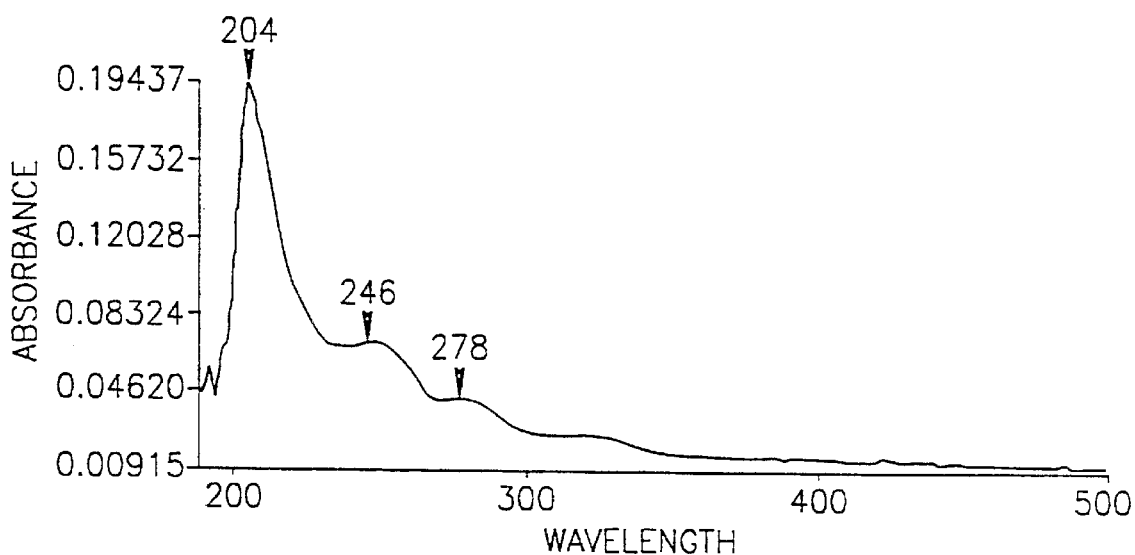
FIG. 9 is a graphic representation showing the UV spectra of bands obtained by separating by thin layer chromatography (TLC).
Figure 9B:
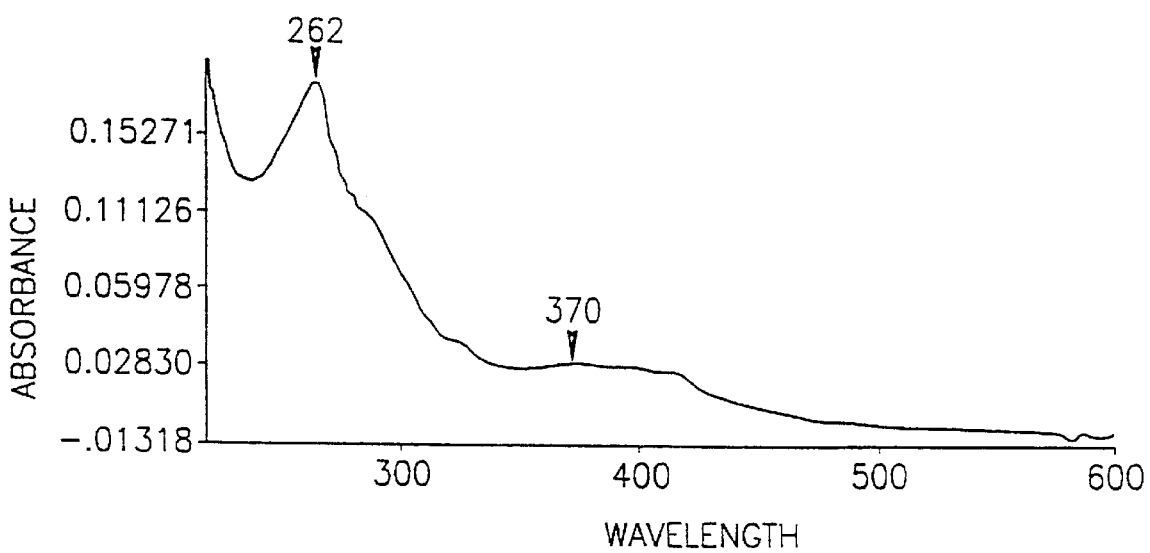
Figure 9C:
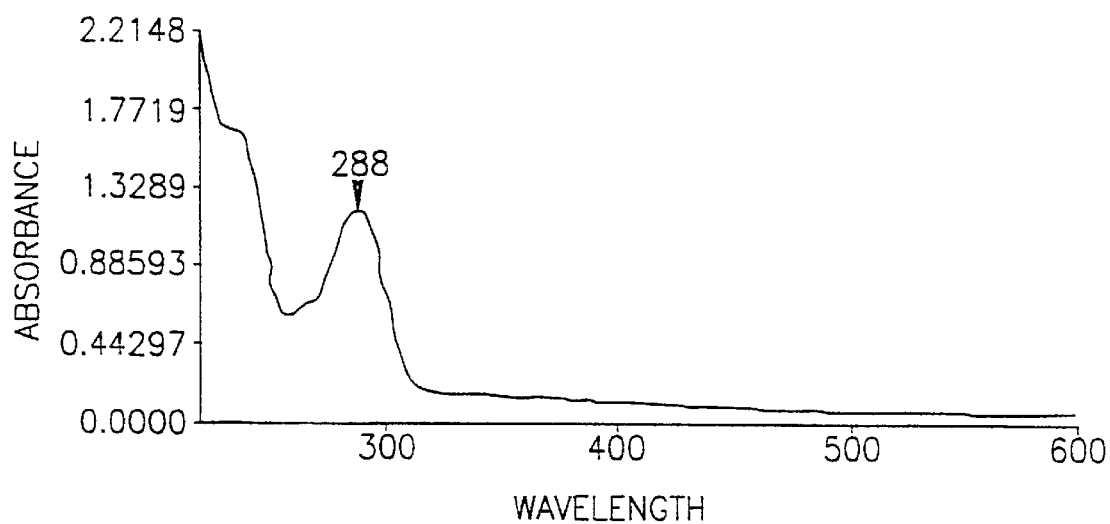
Figure 9D:
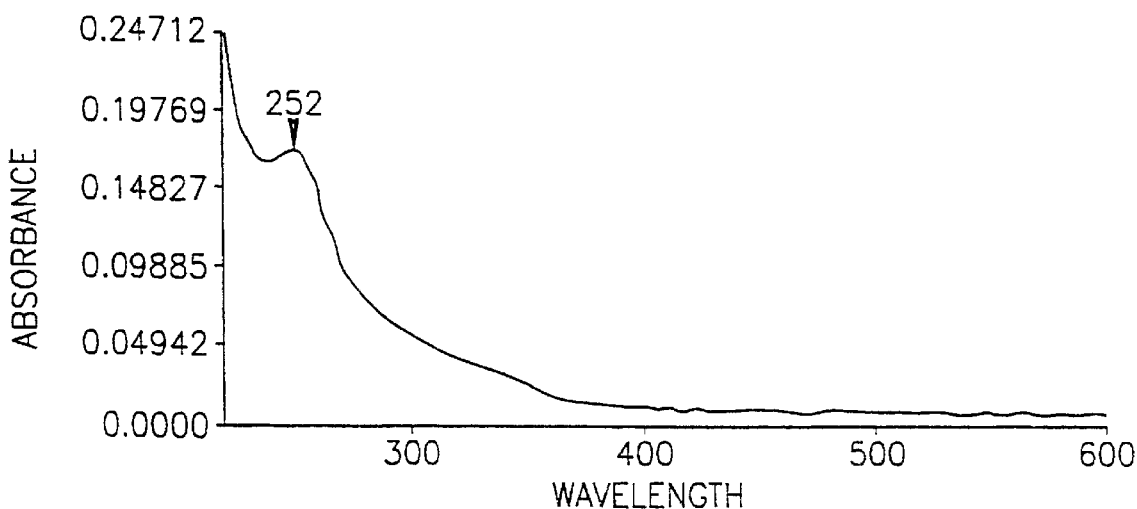

As seen in FIGS. 8A and B and FIGS. 8E and F, Narcissus derived DC (IBR-1) and Artemia derived DC (IBR-4) increased the percent of cells being in the S and $G_2+M$ phases (seen mainly five days after beginning of incubation) as compared to the same cell cultures incubated with water. Against this, as seen in FIGS. 8C and D, incubation of the cells with Narcussis derived AE (IBR-3) had no effect. None of the tested extracts increased the percent of apoptosis in the fibroblast cell cultures.

The effect of the various DCs on the keratinocyte and fibroblast cultures was time and dose dependent.

Example XIII

Effect of DC Preparations Obtained From Bulbs of Various Plants on Growth of Germinated Cucumber Seeds (a) Extracts were prepared from bulbs of various plants as described in Example 1 above. The extracted bulbs were in their dormant stage in which no growth tip could be visualized. The extract concentration is defined as original weight of bulb (gr) per final extract volume (ml).

(b) The effect of extracts on growth of cucumber germinated seeds:

The experimental assay was carried out as explained in Example 1 above. The effect of the tested bulb extracts on the growth of cucumber seeds was tested 24 hours and 48 hours after beginning of the incubation of the extracts with the seeds.

The inhibitive effect of the tested extracts was calculated as described in the Examples above.

Results:

As seen in Table 9 below, most of the extracts showed good inhibitory effect on the growth of the germinated cucumber seeds (up to about 60% inhibition in average). Several of the plants showed very good inhibition activity of about 90% inhibition (e.g. *Pancratium maritumum*). Several of the extracts showed a low inhibitory effect which may, in some cases, be due to the fact that the bulbs were not in full dormancy.

The effect of the extracts from *Pancratium maritumum* and *Hyancinth carnegie* were tested further for their effect on the cucumber seed growth by adding various concentrations of the extracts to the seeds. The results (not shown) showed correlation between the concentration of the added extract and the inhibition effect of the extract on the growth germinated cucumber seeds.

TABLE 9

Inhibition (%) of seed growth by extracts:

| Extract Source | | 24 hours | | 48 hours | |
|---|---|---|---|---|---|
| | | Root (% inhibition) | Hypocotyl (% inhibition) | Root (% inhibition) | Hypocotyl (% inhibition) |
| Sparaxis | 0.52 gr./ml | 38 | −33 | 49 | 39 |
| Hyacinth carnegie | 0.40 gr./ml | 9 | 91 | 94 | 91 |
| Freesia | 0.42 gr./ml | 62 | 18 | 77 | 7 |
| Crocus | 0.41 gr./ml | 48 | 9 | 30 | 37 |
| Ornithogalum arabicum | 0.82 gr./ml | 52 | −18 | 54 | −20 |
| Montbartia | 0.64/gr./ml | 49 | 28 | 63 | 66 |
| Scilla hyacinthus | 1.25 gr./ml | 61 | 0 | 68 | 6 |
| Pancratium maritumum | 0.71 gr./ml | 90 | 89 | 93 | 96 |

− indicates growth stimulation

Example XIV

Effect of Extracts From Narcissus Bulbs on Growth of Cucumber Plants (a) Extracts from dormant Narcissus bulbs were prepared as explained in Example 1 above.

(b) Cucumber seeds were germinated and let grow for three days until they had roots and the hypocotyl of about 4 cm. The plants were then planted in soil and let grow at 23° C. in tap water. The plants were divided into the following three groups, each comprising 18 plants:

1. Plants that were irrigated with tap water;
2. Plants that were irrigated with tap water and treated with the Narcissus bulb extract by spraying the extract (5 mg/ml) on the leaves and the growth meristem; and
3. Plants which were irrigated directly with the Narcissus bulb extract (0.2 gr./ml).

The plants were irrigated every day and following one week of treatment, the plants were taken out of the soil and the effect of each treatment was tested by measuring the length of the roots and stems of each plant.

Results:

As seen in Table 10 below, application of the dormant Narcissus bulb extract on to cucumber plants both by spraying the extract on the leaves and growth meristem (Group 2) as well as by irrigating the plants with the extract (Group 3) resulted in inhibition of the cucumber plants' growth as compared to their growth with tap water.

TABLE 10

Effect of dormant Narcissus bulb extract on growth of cucumber plants

| | % inhibition | |
|---|---|---|
| Irrigation with: | Root | Stem |
| (1) Tap water | 0 | 0 |
| (2) Narcissus bulb extxact applied on leaves and growth center | 21% | 25% |
| (3) Narcissus bulb extract applied with irrigation | 30% | 21% |

Example XV

Effect of Narcissus Bulb Extract on the Growth of Different Types of Seeds (a) The dormant Narcissus bulb extract was prepared as explained above.

(b) Several kinds of seeds (tomato, cabbage, melon, water melon, wheat, grass, cucumber, bean, barley, corn and pea)

were washed overnight with water and then let germinate for 24 hrs at 30° C. in the dark on water soaked filter paper. After 24 hrs the germinated seeds (20 in each experiment set) were applied to a Petri dish with Watman filter paper soaked with the dormant extract.

Each group of seeds was divided into the following groups:

1. Seeds grown in water (control); and
2. Seeds grown with the dormant Narcissus bulb extract.

Various types of seeds were grown with the water or extract (at several concentrations) as explained in Example 1 above and following incubation, the length of the roots and hypocotyls of each seed was measured every 24 hours, depending on the rate of germination and growth. The inhibition effect of the extract tested and calculated as explained above.

As seen in Table 11 below, the dormant Narcissus bulb extract effectively inhibited the growth of the above seeds. The inhibition was to different extents.

TABLE 11

Effect of dormant Narcissus on growth of different types of seeds

| | | % Inhibition | |
|---|---|---|---|
| Seed | DC Concentration | Roots | Hypocotyl |
| Grass | 0.02 | 100 | 72 |
| Water melon | 0.02 | 42 | 74 |
| Cabbage | 0.02 | 63 | 82 |
| Cucumber | 0.2 | 93 | 76 |
| Cucumber | 0.05 | 70 | 72 |
| Cucumber | 0.02 | 52 | 79 |
| Barley | 0.2 | 84 | 21 |
| Barley | 0.05 | 81 | 0 |
| Corn | 0.2 | 70 | 1 |
| Peas | 0.2 | 61 | 69 |
| Peas | 0.05 | 38 | 28 |
| Beans | 0.2 | 79 | 55 |
| Beans | 0.05 | 55 | 13 |
| Beans | 0.02 | 42 | 5 |

Example XVI
Isolation and Identification of an Active Ingredient in the Narcissus Bulb Extract Several grams of powder prepared from active and dormant Narcissus bulbs were extracted with acetone methanol (90:10). The extracts separated using Thin Layer Chromatography (TLC) techniques. The separation was conducted on TLC plates (Silica gel 60 F254 from Merck). Running conditions were water: n-butanol:acetic acid (5:4:1). The detection method was UV light at 254 nm and 365 nm. The bands resulting from the separation were scraped with the silica from the plate, washed with methanol and dried at 60° C. The bands appearing in the extracts from the active Narcissus bulbs were compared to those in the extracts of the dormant Narcissus bulbs.

Results:

Comparison of the bands appearing in the above extract showed that there was a difference in the expression of two bands (termed "band 4" and "band 6") which appeared at a higher concentration in extracts of the dormant bulbs.

The UV absorption spectrum of the two bands and their inhibitive activity on germinated cucumber seeds was tested as explained above.

As seen in FIG. 14, the UV absorption peak of band 4 was at 288 nm and that of band 6 was at 252 nm. As seen in Table 12 below, bands 4 and 6 significantly inhibited the growth of germinated cucumber seeds.

TABLE 12

| Band separated by TLC | 4 | 6 |
|---|---|---|
| UV spectra (nm) in Methanol | 288 | 252 |
| Inhibition (%) (2 mg. dry purified compound/ml) | | |
| 24 hrs | | |
| Hypocotyl | 58 | 58 |
| Root | 87 | 89 |
| 48 hours | | |
| Hypocotyl | 60 | 77 |
| Root | 90 | 94 |

Example XVII
Testing for Toxicity of DC Obtained From Dormant Narcissus Bulbs

The toxicity of DC of the invention was tested using the following methods::

1 Acute Oral Toxicity (Fixed Dose) Test in Rats

The acute oral toxicological test was based on the protocol, code P/ACU/005, issued at January 1996 by Inveresk Research International (IRI), Tranent, EH33 2NE, Scotland.

2. Ames Test

*Salmonella typhimurium* mammalian microsome plate incorporation assay was based on Ames B. N., McCann, J., and Yamasaki E., *Mutation Research,* 31:347–364 (1975).

3. Cytoxicity

Cytoxicity of the extract (5%) of 0.2 gr/ml extract in cosmetic cream, determined by agarose diffusion method was tested by EVIC-CEBA, Bordeaux, France.

4. Irritation potential

Irritation potential of the product in cream ((5%) of 0.2 gr/ml extract) was determined by means of the HET-CAM test (Chorioallantoic membrane of hen's egg) by EVIC-CEBA, Bordeaux, France.

5. Cutaneous Tolerance

Cutaneous tolerance of the extract ((5%) of 0.2 gr/ml extract) in cosmetic cream, after repeated application to the skin was assessed by EVIC-CEBA, Bordeaux, France.

Results:

The results of the toxicity testings using the above methods were as follows:

1. The Acute Oral Toxicity (fixed dose) test in rats oral LD 50>2000 mg/kg body weight, has no acute harmful effects on both young female and male rats.
2. Ames test up to the top-limit dose of 5000 µg/plate, exhibiting no precipitate and no toxicity, did not induce any mutagenic effects on the Ames test.
3. Irritation potential in cream ((5%) of 0.2 gr/ml extract). The product was found as a normally irritant for this kind of product.
4. Cytotoxicity determination by agarose diffusion method of the product in cream ((5%) of 0.2 gr/ml extract) seems to be low and considered to be low and considered normal for this kind of product.
5. Cutaneous tolerance—The clinical assessment of cutaneous tolerance of the extract in cosmetic cream was tested. The product was found very well tolerated by the skin.

Example XVIII
The Effect of DC on Elongation of a Tan (a) The Assay:

A cream containing 5% dihydroxyacetone (DHA) was administered on to the forearms of an individual. DHA is a compound capable of coloring the upper layers of the skin which is used in self tanning products. The cream was administered three times until a tan appeared on the forearms.

The tanned area was then divided into the following three parts, each being treated by administration of a different cream twice a day during 17 days:

1. Treatment with a cream comprising 5% of the DC IBR-1;
2. A cream identical to the one used in (1) above but which does not contain IBR-1;
3. A cream comprising alpha hydroxy acid (AHA) (commercially used for skin treatment); and The amount of color on each skin area was measured using a spectro-colorimeter.

The % effect on elongation of the tan was calculated as:

$$\frac{\text{color of tan of treatment } a}{\text{color of tan with no treatment}} - \frac{\text{color of tan after treatment } b}{\text{color of tan with no treatment}} \times 100$$

Figure 10:
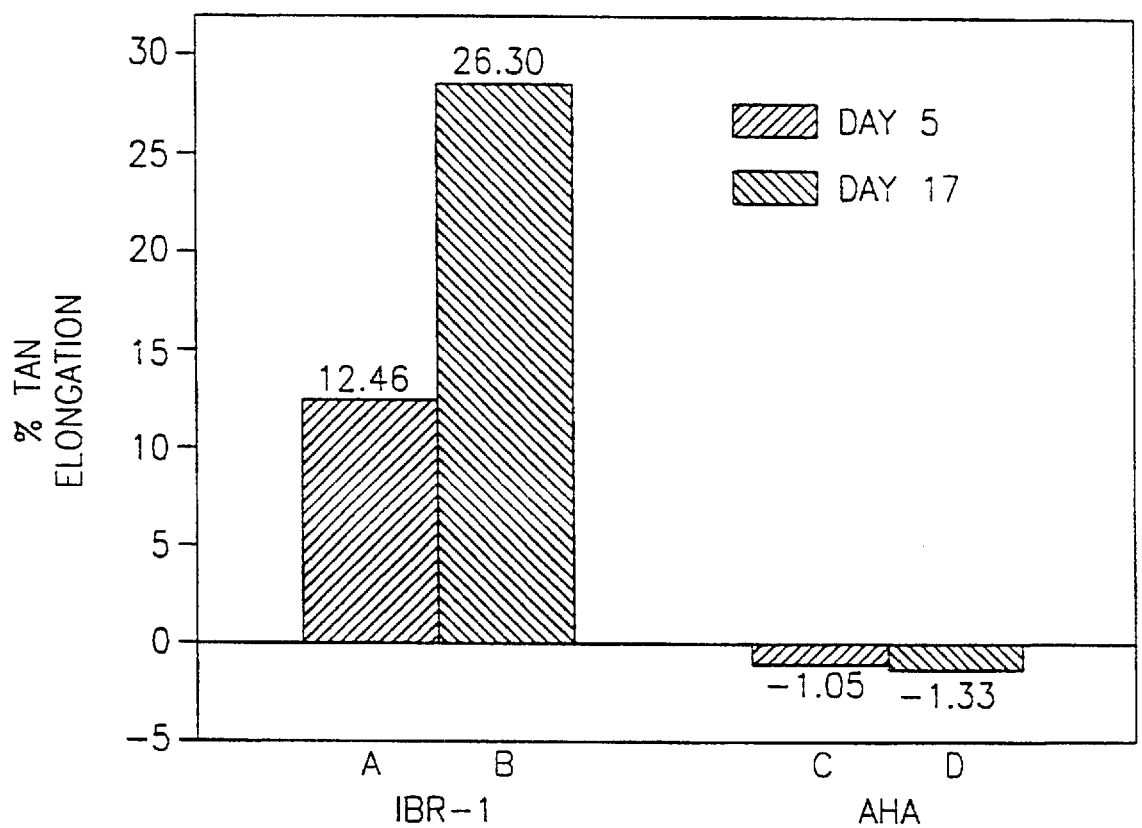
FIG. 10 is a graphic representation showing the comparative effect of different treatments on the duration of a tan 5 days and 17 days after administration of the cream on to the tanned area.

Results:

The results of the above experiment can be seen in FIG. 10, which shows the relation between the effect on the duration of the tan of the cream used in 1 above containing the IBR-1 DC as compared to the effect of the cream which contained no IBR-1 (FIGS. 10A and D) and the relative effect of the cream used in (3) above (comprising AHA) as compared to no cream at all AHA (FIGS. 10C and D). As can be seen in FIG. 10A, 5 days after administration of the creams, the effect of the cream containing IBR-1 on elongation of the tan duration was significantly higher than the effect of the cream which did not contain IBR-1. The effect was even more significant 17 days after administration of the cream as can be seen in FIG. 10B.

FIGS. 10C and D clearly show that the cream used commercially which does not contain IBR-1 had a negative effect on the duration of the tan, i.e. their administration resulted in shorter duration of the tan as compared to no treatment at all. As can also be seen, the cream comprising the AHA shortened the duration of the tan (compared to the duration of the tan with no treatment) 5 days after its administration (FIG. 10C) and 17 days after its administration (FIG. 10D).

The above results show that a cream comprising DC of the invention, most probably due to its inhibition of proliferation of the skin cells, elongates the duration of a tan. Against this, a cream comprising AHA which is commonly used for skin treatment, most probably due to its stimulation of cell division, shortens the duration of the tan.

What is claimed is:

1. A process for producing a purified dorman water extract which inhibits proliferation of target cells or target tissue in diseases and conditions selected from the group consisting of carcinoma, psoriasis, seborrheic keratosis, and wart and/or papilloma infection, comprising:

(a) providing producer cells or producer tissue which is derived from an organism which is zenogeneic to said target cells or target tissue and which is capable of entering into a dormant state, wherein said organism is a plant selected from the group consisting of Narcissus, *Hyacinth carnegie*, Amaryllis, and Pancratium;

(b) inducing said producer cells or producer tissue to enter a dormant state using high temperature, humidity, or combination thereof, or if already in a dormant state, maintaining said state; and (c) conducting a water extraction from the dormant producer cells, dormant producer tissue or from a medium in which said dormant cells or dormant tissue were incubated to obtain a water-soluble dorman extract, whereby, the extract is fractionated so as to obtain a purified dorman extract which is capable of passing through a 0.45 µm filter from said dormant producer cells or dormant producer tissue or from a medium in which said dormant cells or tissue was incubated, and whereby, the extract displays a reversible cell anti-proliferative activity without substantial cytotoxicity, wherein the activity is substantially higher in said fraction than the same fraction obtained from said producer cells or tissue, when in a non-dormant state.

2. A process according to claim 1, wherein said producer tissue is selected from the group consisting of bulbs, roots, corms, rhizomes, buds, seeds, and mixtures thereof.

3. A pharmaceutical or cosmetic composition having an anti-proliferative effect on target cells or target tissue of an individual which comprises:

the purified dorman water extract produced according to the process of claim 1, having an anti-proliferative effect on target cells or target tissue of said individual in need thereof, in combination with a pharmaceutically acceptable carrier or cosmetic composition.

4. A method of treatment of anti-proliferative diseases and conditions selected from the group consisting of carcinoma, psoriasis, seborrheic keratosis, and wart and/or papilloma infection which comprises:

administering to an individual an amount of a composition or cosmetic composition of claim 3 effective to treat said anti-proliferative disease or condition in the individual.

\* \* \* \* \*